US011458032B2

(12) United States Patent
Blecher

(10) Patent No.: US 11,458,032 B2
(45) Date of Patent: Oct. 4, 2022

(54) ANATOMICAL BRACE FOR DYNAMICALLY STABILIZING THE PATELLA DURING KNEE ARTICULATION SO AS TO ADDRESS PATELLA TRACKING ERROR

(71) Applicant: Sports Medicine Sciences, LLC, Encino, CA (US)

(72) Inventor: Andrew M. Blecher, Encino, CA (US)

(73) Assignee: Sports Medicine Sciences, LLC, Encino, CA (US)

( * ) Notice: Subject to any disclaimer, the term of this patent is extended or adjusted under 35 U.S.C. 154(b) by 1520 days.

(21) Appl. No.: 15/061,379

(22) Filed: Mar. 4, 2016

(65) Prior Publication Data

US 2016/0256310 A1 Sep. 8, 2016
US 2017/0281388 A9 Oct. 5, 2017

Related U.S. Application Data

(63) Continuation-in-part of application No. 14/738,774, filed on Jun. 12, 2015, now Pat. No. 10,617,550.
(Continued)

(51) Int. Cl.
*A61F 5/01* (2006.01)
(52) U.S. Cl.
CPC .... *A61F 5/0123* (2013.01); *A61F 2005/0167* (2013.01); *A61F 2005/0176* (2013.01); *A61F 2250/0073* (2013.01)
(58) Field of Classification Search
CPC ........ A61F 5/0123; A61F 5/01; A61F 5/0102; A61F 5/0104; A61F 5/0106; A61F 5/0125; A61F 5/013; A61F 5/058; A61F 5/05825; A61F 5/05841; A61F 5/0585; A61F 2005/0167; A61F 2005/0176; A61F 2005/0134; A61F 2005/0137; A61F 2005/0141; A61F 2005/0144; A61F 2005/0146; A61F 2005/0148;
(Continued)

(56) References Cited

U.S. PATENT DOCUMENTS 2,195,024 A 3/1940 Bullock
4,296,744 A 10/1981 Palumbo
(Continued)

FOREIGN PATENT DOCUMENTS

| CA | 2831507 | 4/2015 |
|---|---|---|
| EP | 2 727 565 | 5/2014 |
| WO | WO 2009/126724 | 10/2009 |

OTHER PUBLICATIONS

Elastic definition, Dictionary.com, definition 1, https://www.dictionary.com/browse/elastic (Year: 2020).*
(Continued)

*Primary Examiner* — Ophelia A Hawthorne
(74) *Attorney, Agent, or Firm* — Pandiscio & Pandiscio

(57) ABSTRACT

An anatomical brace for dynamically stabilizing the patella during knee articulation so as to address patella tracking error, the anatomical brace being configured such that, when the anatomical brace is mounted to the knee of a patient, and when the knee thereafter moves to full extension, the anatomical brace applies a proximal/medial force to the patella of the patient, and when the knee thereafter moves to full flexion, the proximal/medial force is released.

49 Claims, 17 Drawing Sheets

Related U.S. Application Data

(60) Provisional application No. 62/127,919, filed on Mar. 4, 2015, provisional application No. 62/018,575, filed on Jun. 28, 2014.

(58) Field of Classification Search
CPC ...... A61F 2005/0151; A61F 2005/0153; A61F 2005/0155; A61F 2005/0165; A61F 2005/0169
See application file for complete search history.

(56) References Cited

U.S. PATENT DOCUMENTS

| | | | |
|---|---|---|---|
| 4,370,977 A | 2/1983 | Mauldin et al. | |
| 4,370,978 A | 2/1983 | Palumbo | |
| 4,397,308 A | 8/1983 | Hepburn | |
| 4,423,720 A | 1/1984 | Meier et al. | |
| 4,445,505 A | 5/1984 | Labour et al. | |
| 4,489,718 A | 12/1984 | Martin | |
| 4,508,111 A | 4/1985 | Hepburn | |
| 4,607,628 A | 8/1986 | Dashefsky | |
| 4,657,000 A | 4/1987 | Hepburn | |
| 4,682,776 A | 7/1987 | Mitchell et al. | |
| 4,733,656 A | 3/1988 | Marquette | |
| 4,805,606 A | 2/1989 | McDavid, III | |
| 5,002,045 A | 3/1991 | Spademan | |
| 5,024,216 A | 6/1991 | Shiono | |
| 5,112,045 A | 5/1992 | Mason et al. | |
| 5,277,697 A | 1/1994 | France et al. | |
| 5,303,716 A | 4/1994 | Mason et al. | |
| 5,383,845 A | 1/1995 | Nebolon | |
| 5,472,410 A | 12/1995 | Hamersly | |
| 5,509,894 A | 4/1996 | Mason et al. | |
| 5,562,605 A | 10/1996 | Taylor | |
| 5,575,764 A | 11/1996 | Van Dyne | |
| 5,599,288 A * | 2/1997 | Shirley ................ | A61F 5/0123 602/16 |
| 5,613,943 A | 3/1997 | Palumbo | |
| 5,624,390 A | 4/1997 | Van Dyne | |
| 5,672,152 A | 9/1997 | Mason et al. | |
| 5,683,353 A | 11/1997 | Hamersly | |
| 5,759,167 A | 6/1998 | Shields, Jr. et al. | |
| 5,772,618 A | 6/1998 | Mason et al. | |
| 5,797,864 A | 8/1998 | Taylor | |
| 5,807,294 A | 9/1998 | Cawley et al. | |
| 5,827,208 A | 10/1998 | Mason et al. | |
| 5,857,988 A | 1/1999 | Shirley | |
| 5,865,776 A | 2/1999 | Springs | |
| 6,001,075 A | 12/1999 | Clemens et al. | |
| 6,110,138 A | 8/2000 | Shirley | |
| 6,129,690 A | 10/2000 | Hamlin et al. | |
| 6,245,034 B1 | 6/2001 | Bennett et al. | |
| 6,287,269 B1 | 9/2001 | Osti et al. | |
| 6,471,664 B1 | 10/2002 | Campbell et al. | |
| 6,551,264 B1 | 4/2003 | Cawley et al. | |
| 6,635,024 B2 | 10/2003 | Hatton et al. | |
| 6,719,713 B2 | 4/2004 | Mason | |
| 6,936,019 B2 | 8/2005 | Mason | |
| 7,004,919 B2 | 2/2006 | Gaylord et al. | |
| 7,059,329 B2 | 6/2006 | Mason et al. | |
| 7,060,045 B2 | 6/2006 | Mason et al. | |
| 7,083,586 B2 | 8/2006 | Simmons et al. | |
| 7,189,212 B2 | 3/2007 | Popp et al. | |
| 7,192,407 B2 | 3/2007 | Seligman et al. | |
| 7,207,960 B2 | 4/2007 | Kenney | |
| 7,235,059 B2 | 6/2007 | Mason et al. | |
| 7,479,122 B2 | 1/2009 | Ceriani et al. | |
| 7,481,785 B2 | 1/2009 | Turrini et al. | |
| 7,485,103 B2 | 2/2009 | Mason et al. | |
| 7,517,330 B2 | 4/2009 | DeHarde et al. | |
| 7,534,217 B2 | 5/2009 | Seligman et al. | |
| 7,811,242 B2 | 10/2010 | Seligman | |
| 7,819,830 B2 | 10/2010 | Sindel et al. | |
| 7,846,115 B2 | 12/2010 | Seligman et al. | |
| 7,867,183 B2 | 1/2011 | Kazmierczak | |
| 7,905,851 B1 | 3/2011 | Bledsoe | |
| 8,123,709 B2 | 2/2012 | DeHarde et al. | |
| 8,172,781 B2 | 5/2012 | Oddou et al. | |
| 8,273,045 B2 | 9/2012 | Ceriani | |
| 8,277,403 B2 | 10/2012 | Ceriani et al. | |
| 8,376,974 B2 | 2/2013 | Nace | |
| 8,419,670 B2 | 4/2013 | Downing | |
| 8,435,197 B2 | 5/2013 | Vollbrecht et al. | |
| 8,882,688 B1 | 11/2014 | Ancinec | |
| 8,945,031 B2 | 2/2015 | Cardinali | |
| 9,095,418 B2 | 8/2015 | Cardinali et al. | |
| 9,113,998 B2 | 8/2015 | Romo | |
| 9,132,026 B2 | 9/2015 | Bledsoe et al. | |
| 2002/0133108 A1* | 9/2002 | Jagodzinski ............ | A61F 5/0123 602/16 |
| 2003/0144620 A1 | 7/2003 | Sieller et al. | |
| 2008/0249448 A1 | 10/2008 | Stevenson et al. | |
| 2011/0098618 A1* | 4/2011 | Fleming ................ | A61F 5/0123 602/16 |
| 2011/0137220 A1 | 6/2011 | Vollbrecht et al. | |
| 2013/0110020 A1* | 5/2013 | Ingimundarson ..... | A61F 5/0123 602/16 |
| 2013/0172797 A1* | 7/2013 | Merkley ................ | A61F 5/01 602/16 |
| 2013/0245523 A1* | 9/2013 | Romo ................ | A61F 5/0123 602/16 |
| 2014/0068838 A1 | 3/2014 | Beers et al. | |
| 2014/0276305 A1 | 9/2014 | Cardinali et al. | |
| 2014/0276311 A1 | 9/2014 | Hollister et al. | |
| 2014/0336554 A1 | 11/2014 | Romo et al. | |
| 2015/0119777 A1* | 4/2015 | Garrish ................ | A61F 5/0123 602/16 |
| 2015/0126917 A1 | 5/2015 | Stier | |
| 2015/0133839 A1 | 5/2015 | Roebelt et al. | |
| 2015/0374531 A1 | 12/2015 | Fedon | |
| 2015/0374532 A1 | 12/2015 | Fedon | |
| 2019/0029860 A1 | 1/2019 | Blecher | |

OTHER PUBLICATIONS

Stillwell, William, M.D., The VMO—The Key to Patella Tracking, Knee Pain Relief and Knee Joint Stability, EzineArticles, Nov. 24, 2008.
Bauerfeind USA Inc., Sports Ebow Brace, 2016, https://www.bauerfeind.com/b2c/Sports-Brace/Sports-Elbow-Brace/p/YPBF_BAE_EPITRPOWG.
Bellacure, Relieving pain. Restoring lifestyle., 2010, https://bellacure.com/en/products/index.html.
Breginc, https://www.youtube.com/watch?v=FgBbbAjdSj4 (published on Jul. 30, 2012).
Breginc, https://www.youtube.com/watch?v=fr0Q5QK0060 (published on Sep. 17, 2014).
Breginc, https://www.youtube.com/watch?v=AARHoQ1xJXg&sns=em (published on Jul. 28, 2014).
Breg, Inc., FreeRunner Knee Brace, 2016, http://www.breg.com/products/knee-bracing/patellofemoral/freerunner-knee-brace.

* cited by examiner

ANATOMICAL BRACE FOR DYNAMICALLY STABILIZING THE PATELLA DURING KNEE ARTICULATION SO AS TO ADDRESS PATELLA TRACKING ERROR

REFERENCE TO PENDING PRIOR PATENT APPLICATION

This patent application is also a continuation-in-part of prior U.S. patent application Ser. No. 14/738,774, filed Jun. 12, 2015 by Breg, Inc. and Shane C. Fedon et al. for KNEE BRACE HAVING A VARIABLE TENSIONING OFFSET CAM, which in turn claims benefit of prior U.S. Provisional Patent Application Ser. No. 62/018,575, filed Jun. 28, 2014 by Breg, Inc. and Shane C. Fedon et al. for KNEE BRACE HAVING A VARIABLE TENSIONING OFFSET CAM.

FIELD OF THE INVENTION

This invention relates to anatomical braces in general, and more particularly to anatomical braces for dynamically stabilizing the patella during knee articulation so as to address patella tracking error.

BACKGROUND OF THE INVENTION

The knee joint is formed at the convergence of the femur and the tibia. The patella (also known as the knee cap) sits on the anterior side of the knee joint, at the base of the femur. The patella and the femur together form another joint, i.e., the patello-femoral joint. At the patello-femoral joint, the posterior side of the patella (formed as a ridge) engages the anterior side of the femur (formed as a groove). With a properly functioning patello-femoral joint, the patella ridge rides in the femoral groove as the knee articulates. Among other things, with a properly functioning patello-femoral joint, the patella moves from distal (in flexion) to proximal (in extension).

Many people suffer from improper tracking of the patella relative to the femur. More particularly, many people suffer from "patella tracking error" where the patella fails to track properly along the femur as the knee articulates. In many cases, with patella tracking error, the patella improperly tracks laterally as the knee moves from flexion to extension, and/or the patella fails to track proximally as the knee moves from flexion to extension. Less severe forms of patella tracking error can cause pain in the joint. More severe forms of patella tracking error can lead to cartilage damage and arthritis of the knee.

As a result, a recognized need exists for effective treatment of patella tracking errors.

In U.S. Pat. No. 6,551,264, issued Apr. 22, 2003 to Cawley et al. for ORTHOSIS FOR DYNAMICALLY STABILIZING THE PATELLO-FEMORAL JOINT, there is disclosed an anatomical brace for dynamically stabilizing the patella during knee articulation so as to address patella tracking errors.

While the anatomical brace disclosed in U.S. Pat. No. 6,551,264 is a significant improvement over prior art anatomical braces, it nonetheless suffers from a significant design limitation, i.e., it can impose only lateral-to-medial forces on the patella as the knee moves from flexion to extension, and is unable to impose distal-to-proximal forces (or diagonal forces) on the patella as the knee moves from flexion to extension. As a result, the anatomical brace disclosed in U.S. Pat. No. 6,551,264 is only partially successful in dynamically stabilizing the patella during knee articulation so as to address patella tracking errors.

In addition, the anatomical brace disclosed in U.S. Pat. No. 6,551,264 also suffers from several additional design limitations.

Among other things, the anatomical brace disclosed in U.S. Pat. No. 6,551,264 tends to be relatively heavy and intrusive, inasmuch as it uses a so-called "double hinge construction" in which hinge mechanisms are disposed on both the lateral and medial sides of the knee joint, and includes a substantial body of fabric on the posterior side of the knee which impedes full flexion of the knee (e.g., due to bunching in the back of the brace).

Furthermore, the anatomical brace disclosed in U.S. Pat. No. 6,551,264 can migrate during use, inasmuch as it uses only a single strap to secure the anatomical brace to the calf of the patient and uses only a single strap to secure the anatomical brace to the thigh of the patient.

And it should also be appreciated that the anatomical brace disclosed in U.S. Pat. No. 6,551,264 suffers from the fact that it does not adequately relax the forces applied around the kneecap during knee flexion, and hence the anatomical brace disclosed in U.S. Pat. No. 6,551,264 is "too tight" around the kneecap during knee flexion.

As a result, one object of the present invention is to provide a novel anatomical brace for dynamically stabilizing the patella during knee articulation so as to address patella tracking errors, wherein the anatomical brace is configured to apply distal-to-proximal, as well as lateral-to-medial, forces (i.e., as distal-to-proximal/lateral-to-medial diagonal forces) to the patella as the knee moves from flexion to extension.

And another object of the present invention is to provide a novel anatomical brace which is relatively lightweight and non-intrusive, by eliminating the so-called "double hinge construction", and by avoiding the use of a substantial body of fabric on the posterior side of the knee which could impede full flexion of the knee (e.g., due to bunching in the back of the brace).

And another object of the present invention is to provide a novel anatomical brace which is more resistant to migration during use, by providing a more robust securement to the calf of the patient and by providing a more robust securement to the thigh of the patient.

And another object of the present invention is to provide a novel anatomical brace which relaxes the forces applied to the patella during knee flexion so that the novel anatomical brace is not "too tight" around the kneecap during knee flexion.

SUMMARY OF THE INVENTION

These and other objects are addressed by the present invention, which comprises the provision and use of a novel anatomical brace for dynamically stabilizing the patella during knee articulation so as to address patella tracking errors.

Among other things, the novel anatomical brace is configured to apply distal-to-proximal, as well as lateral-to-medial, forces (i.e., as distal-to-proximal/lateral-to-medial diagonal forces) to the patella as the knee moves from flexion to extension.

And the novel anatomical brace is configured to be relatively lightweight and non-intrusive, by eliminating the so-called "double hinge construction", and by avoiding the use of a substantial body of fabric on the posterior side of the knee which could impede full flexion of the knee (e.g., due to bunching in the back of the brace).

And the novel anatomical brace is configured to be more resistant to migration during use, by providing a more robust securement to the calf of the patient and by providing a more robust securement to the thigh of the patient.

And the novel anatomical brace is configured to relax the forces applied to the patella during knee flexion so that the novel anatomical brace is not "too tight" around the kneecap during knee flexion.

In one preferred form of the invention, there is provided an anatomical brace for dynamically stabilizing the patella during knee articulation so as to address patella tracking error, said anatomical brace comprising:
  a brace body comprising:
    a distal band having a first end, a second end and a fastener for securing together said first end of said distal band and said second end of said distal band;
    a proximal band having a first end, a second end and a fastener for securing together said first end of said proximal band and said second end of said proximal band;
    a medial connector having a distal end and a proximal end, said distal end of said medial connector being connected to said distal band and said proximal end of said medial connector being connected to said proximal band;
    a lateral connector having a distal end and a proximal end, said distal end of said lateral connector being connected to said distal band and said proximal end of said lateral connector being connected to said proximal band;
    said distal band, said proximal band, said medial connector and said lateral connector together defining a central opening sized to receive the patella of a patient;
  a hinge mechanism comprising a distal segment, a proximal segment and a pivot for pivotally connecting said distal segment and said proximal segment, said distal segment of said hinge mechanism being connected to said distal band and said proximal segment of said hinge mechanism being connected to said proximal band;
    a first cable guide mounted to the posterior portion of said pivot;
    a second cable guide mounted to said proximal segment of said hinge mechanism;
    a third cable guide secured to said lateral connector;
    a cable having a first end and a second end;
    said first end of said cable being mounted to said distal segment of said hinge mechanism, said second end of said cable being mounted to at least one of said distal band and said lateral connector, and said cable being routed proximally along said distal segment of said hinge mechanism, through said first cable guide, proximally along said proximal segment of said hinge mechanism, through said second cable guide, laterally along said proximal band, distally along said lateral connector and through said third cable guide;
  wherein, when said anatomical brace is mounted to the knee of a patient so that said distal band is secured to the calf of the patient, said proximal band is secured to the thigh of the patient and the patella of the patient is received in said central opening of said brace body, and when the knee thereafter moves to full extension, said cable is tensioned, whereby to apply a proximal/medial force to the patella of the patient, and when the knee thereafter moves to full flexion, said cable is relaxed, so that the proximal/medial force is released.

In another preferred form of the invention, there is provided a method for dynamically stabilizing the patella during knee articulation so as to address patella tracking error, said method comprising:
  providing an anatomical brace comprising:
    a brace body comprising:
      a distal band having a first end, a second end and a fastener for securing together said first end of said distal band and said second end of said distal band;
      a proximal band having a first end, a second end and a fastener for securing together said first end of said proximal band and said second end of said proximal band;
      a medial connector having a distal end and a proximal end, said distal end of said medial connector being connected to said distal band and said proximal end of said medial connector being connected to said proximal band;
      a lateral connector having a distal end and a proximal end, said distal end of said lateral connector being connected to said distal band and said proximal end of said lateral connector being connected to said proximal band;
      said distal band, said proximal band, said medial connector and said lateral connector together defining a central opening sized to receive the patella of a patient;
    a hinge mechanism comprising a distal segment, a proximal segment and a pivot for pivotally connecting said distal segment and said proximal segment, said distal segment of said hinge mechanism being connected to said distal band and said proximal segment of said hinge mechanism being connected to said proximal band;
      a first cable guide mounted to the posterior portion of said pivot;
      a second cable guide mounted to said proximal segment of said hinge mechanism;
      a third cable guide secured to said lateral connector;
      a cable having a first end and a second end;
      said first end of said cable being mounted to said distal segment of said hinge mechanism, said second end of said cable being mounted to at least one of said distal band and said lateral connector, and said cable being routed proximally along said distal segment of said hinge mechanism, through said first cable guide, proximally along said proximal segment of said hinge mechanism, through said second cable guide, laterally along said proximal band, distally along said lateral connector and through said third cable guide; and
    mounting said anatomical brace to the knee of a patient so that said distal band is secured to the calf of the patient, said proximal band is secured to the thigh of the patient and the patella of the patient is received in said central opening of said brace body;
    such that when the knee thereafter moves to full extension, said cable is tensioned, whereby to apply a proximal/medial force to the patella of the patient, and when the knee thereafter moves to full flexion, said cable is relaxed, so that the proximal/medial force is released.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
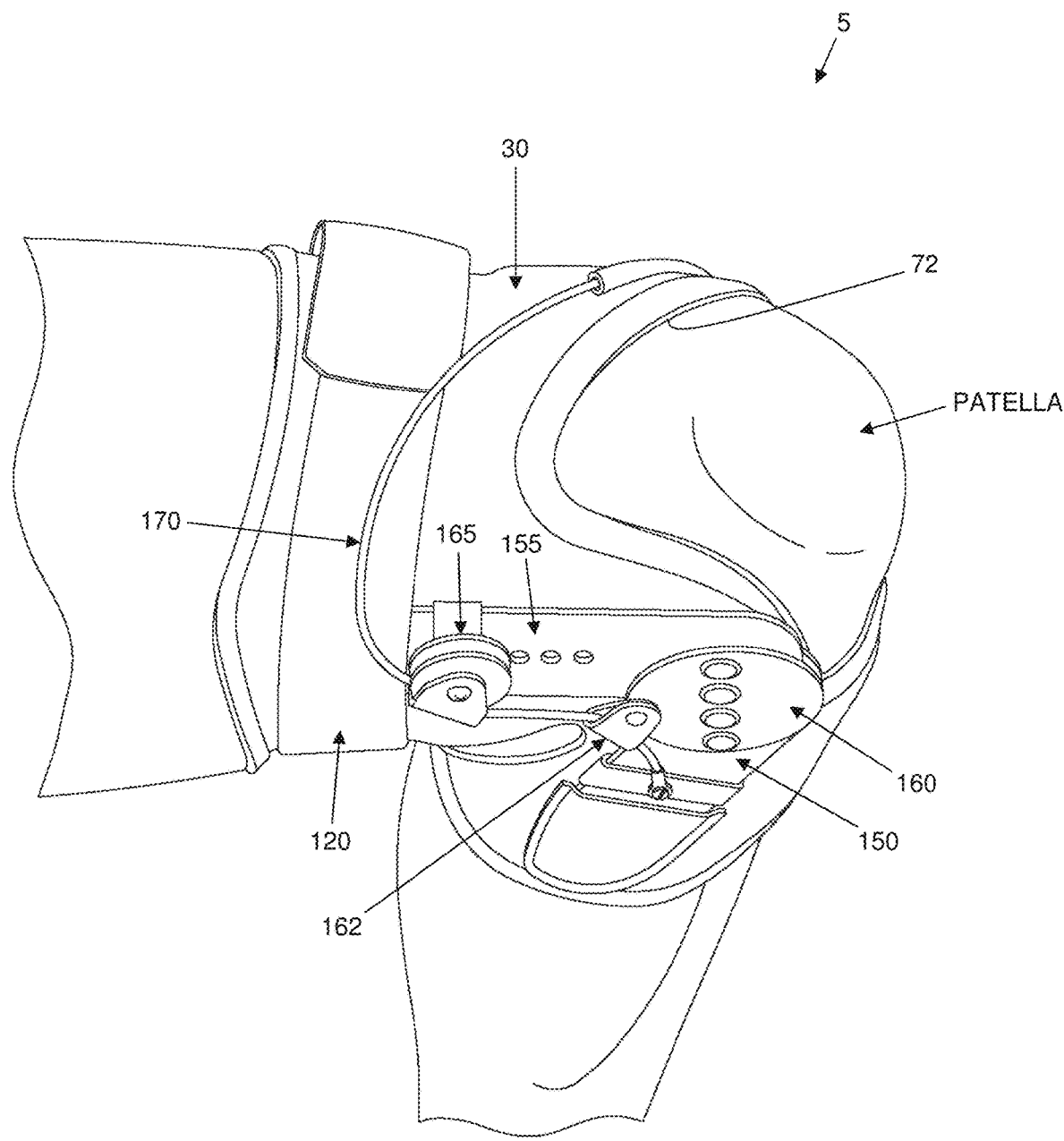
FIG. 1 is a schematic view showing the novel anatomical brace of the present invention from the medial side, with the knee in full flexion.
Figure 2:
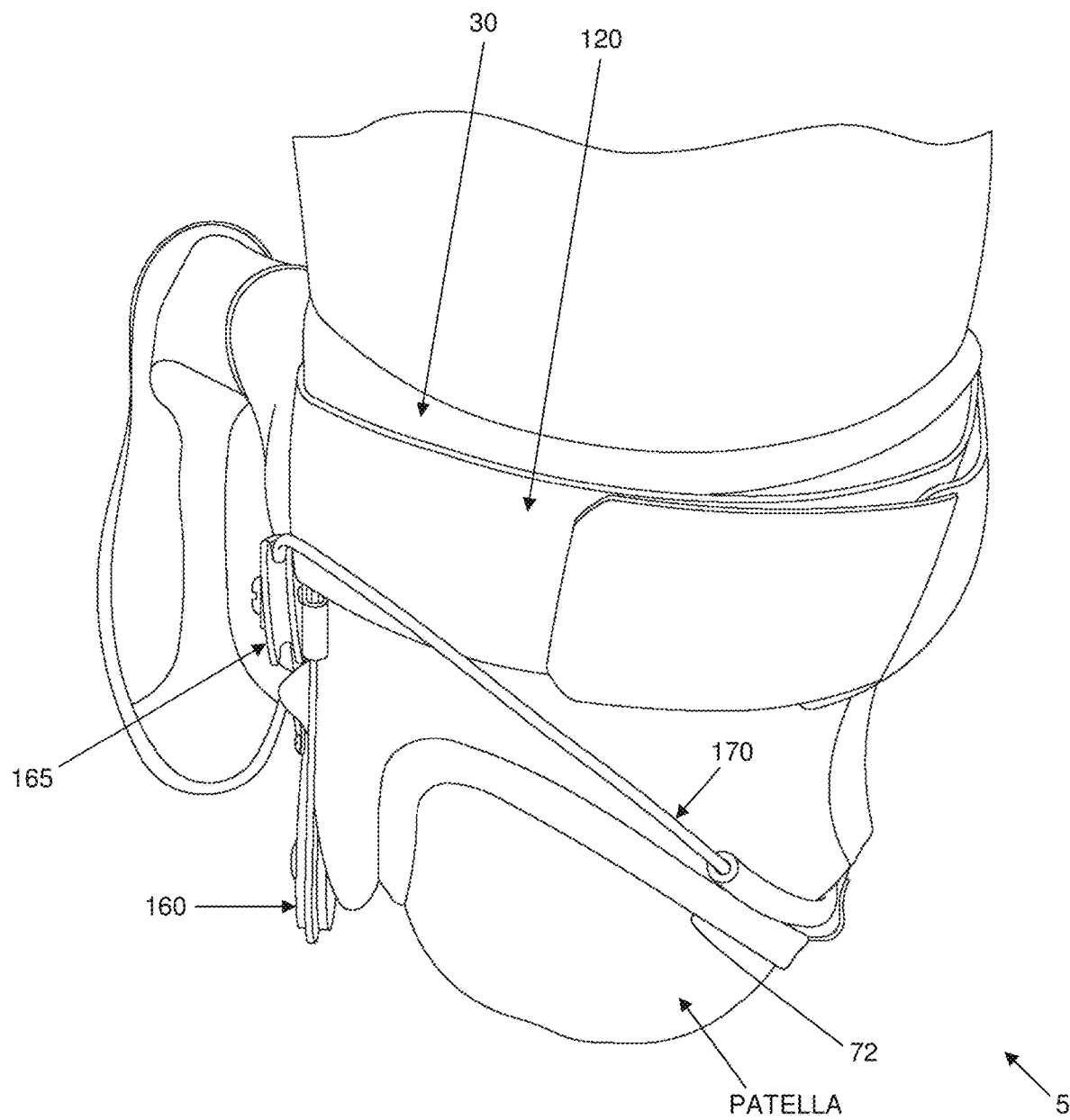
FIG. 2 is a schematic view showing the novel anatomical brace of the present invention from the anterior side, with the knee in full flexion.
Figure 3:
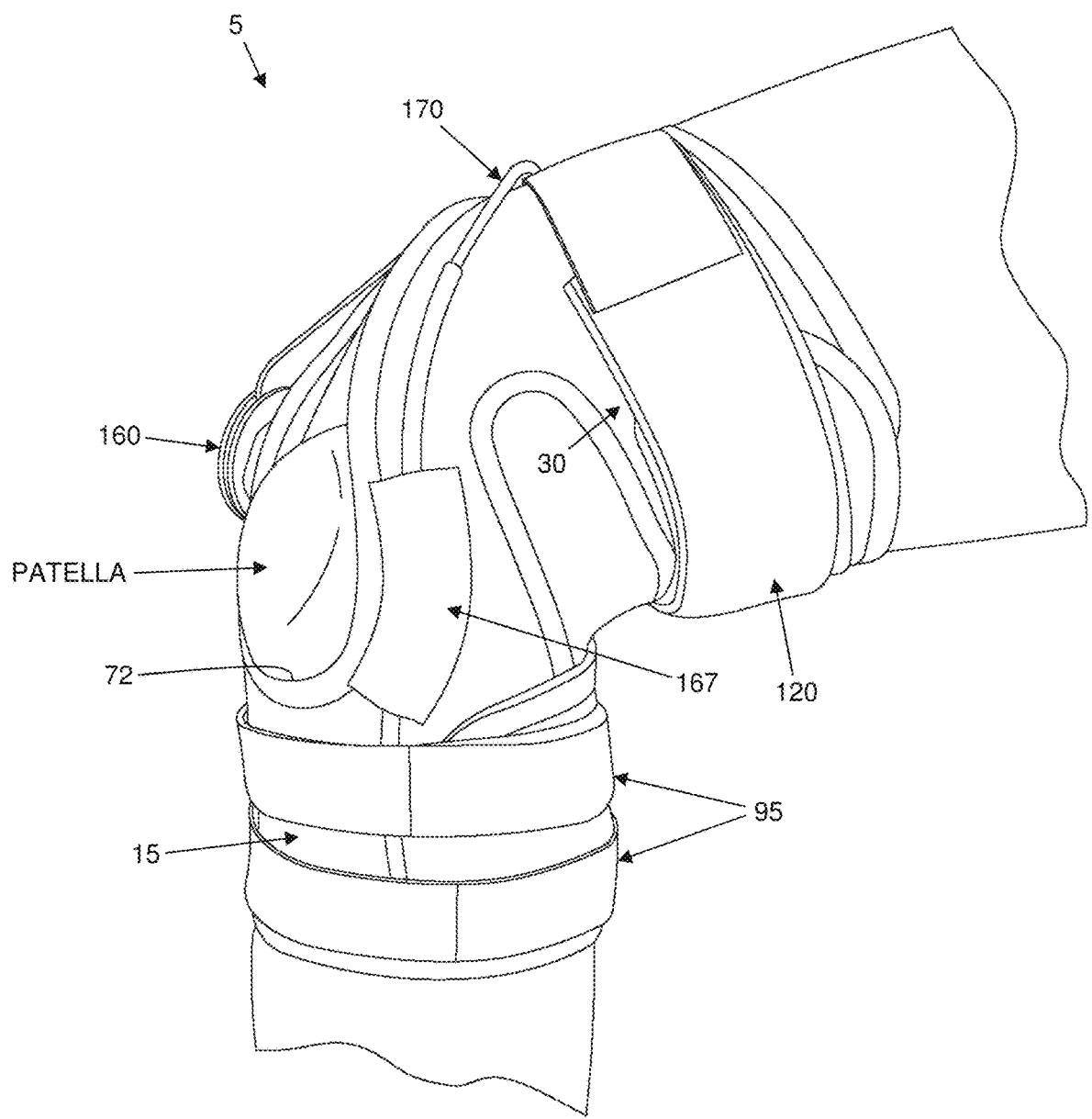
FIG. 3 is a schematic view showing the novel anatomical brace of the present invention from the lateral side, with the knee in full flexion.
Figure 4:
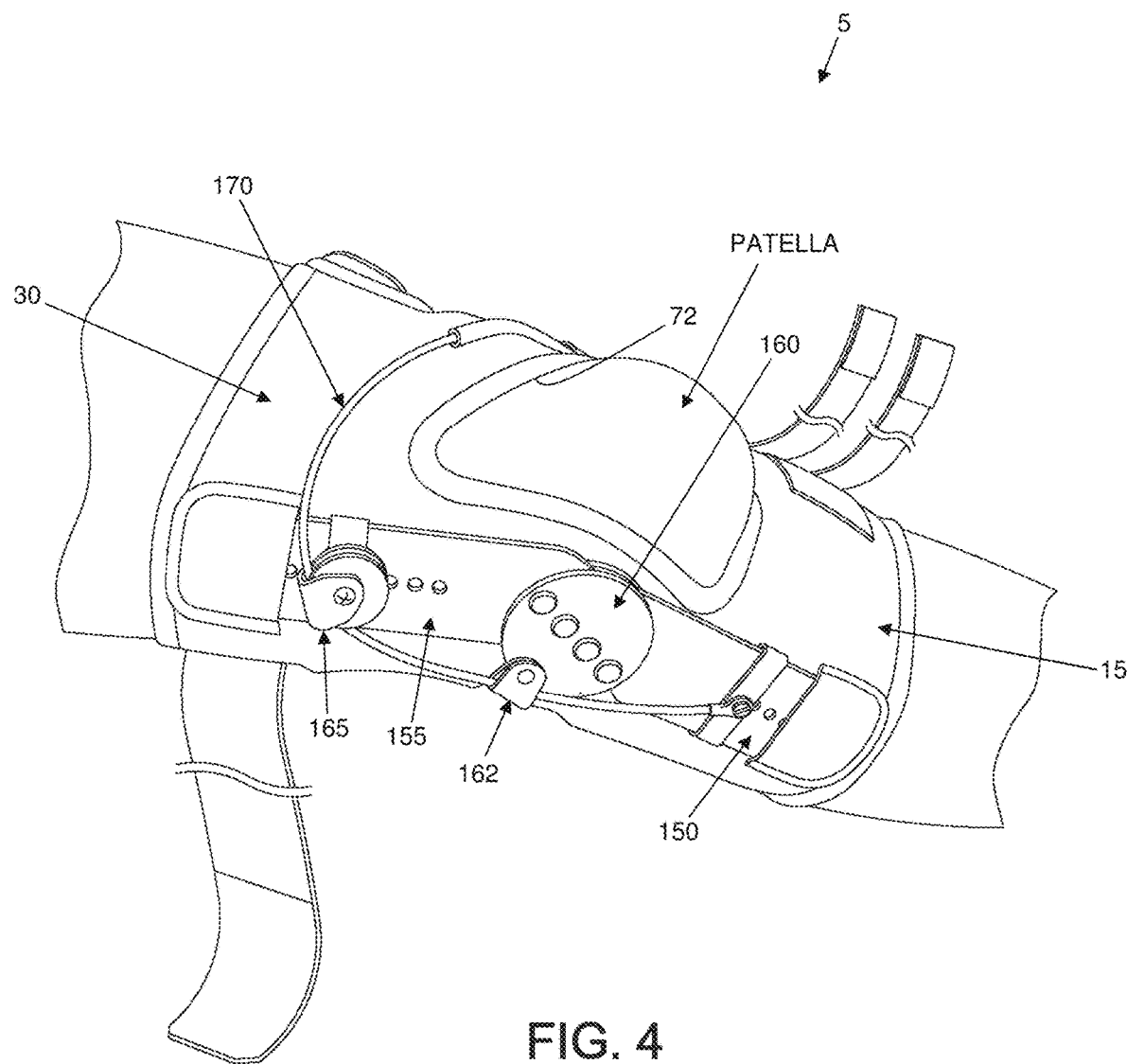
FIG. 4 is a schematic view showing the novel anatomical brace of the present invention from the medial side, with the knee in full extension.
Figure 5:
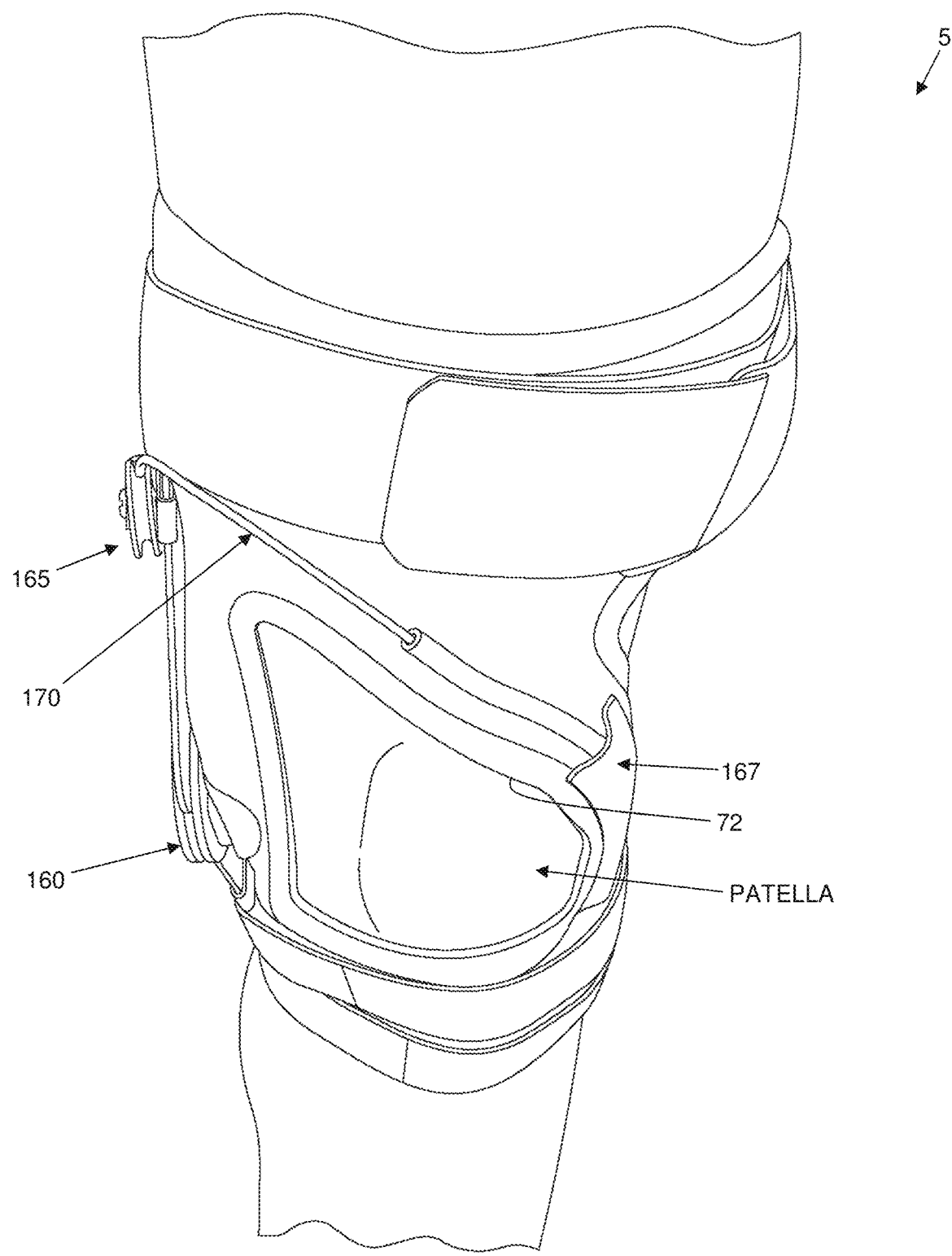
FIG. 5 is a schematic view showing the novel anatomical brace of the present invention from the anterior side, with the knee in full extension.
Figure 6:
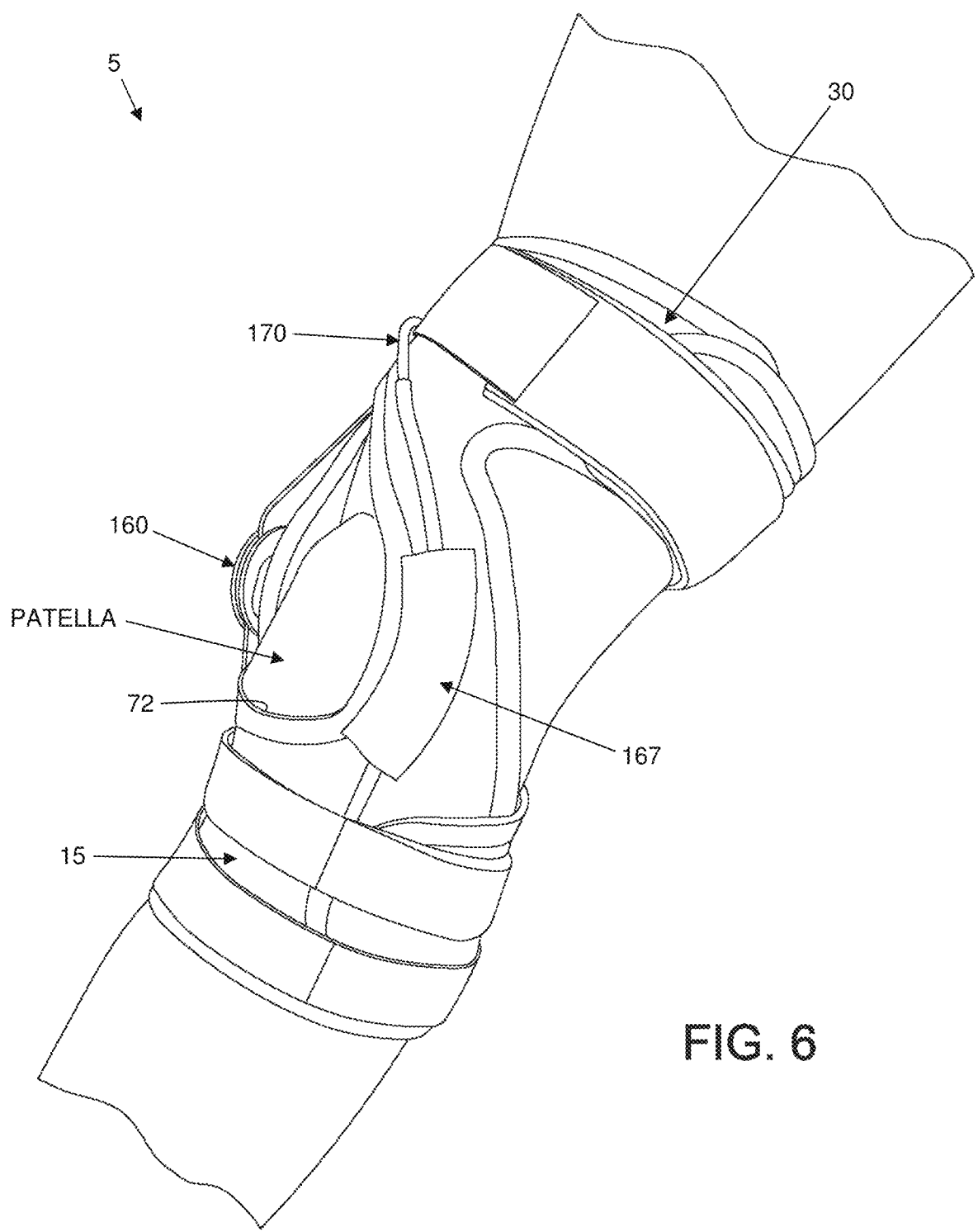
FIG. 6 is a schematic view showing the novel anatomical brace of the present invention from the lateral side, with the knee in full extension.
Figure 7:
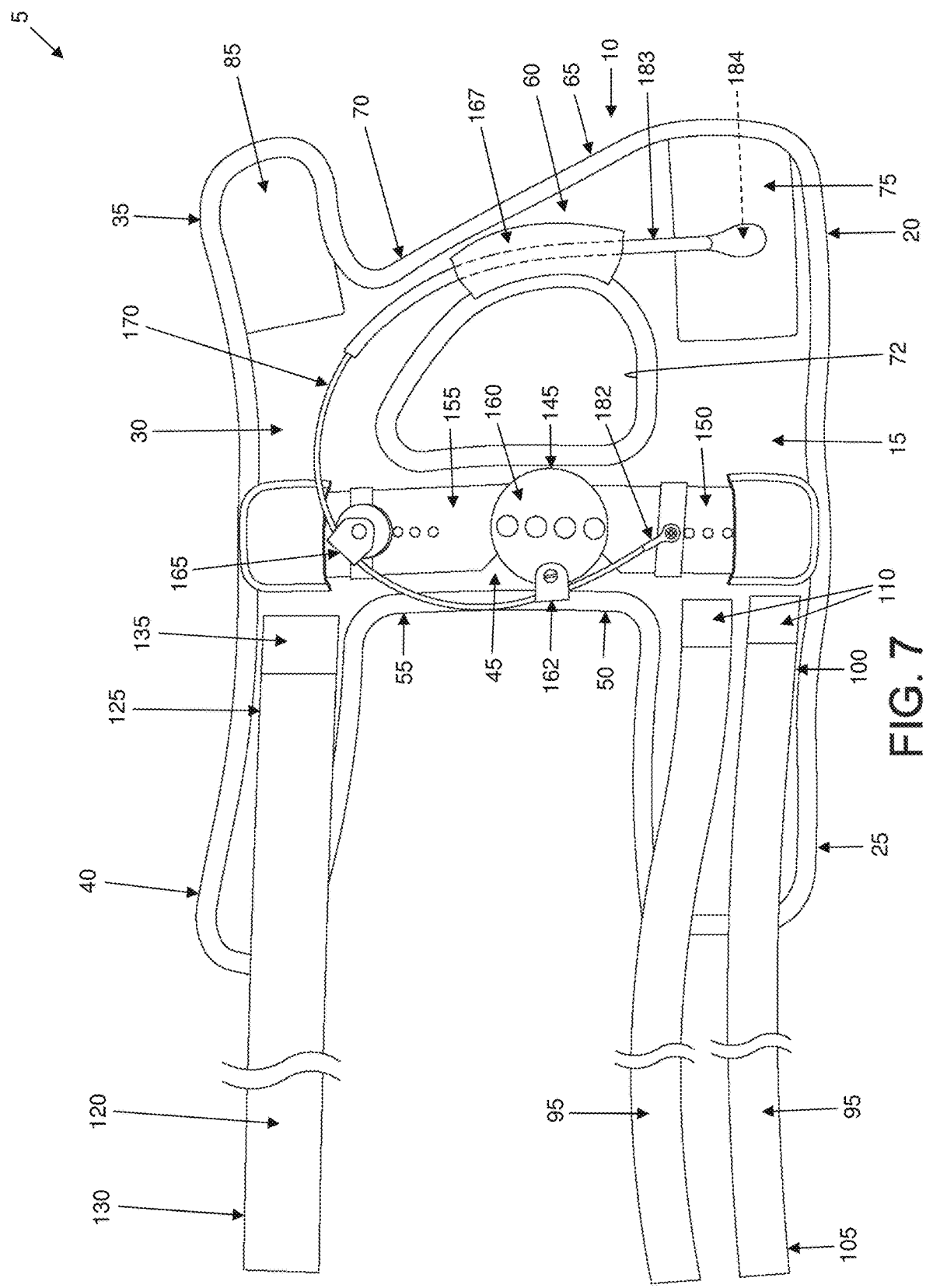
FIG. 7 is a schematic view showing the front (anterior) side of the novel anatomical brace of the present invention, with the anatomical brace laid out flat on a surface.
Figure 8:
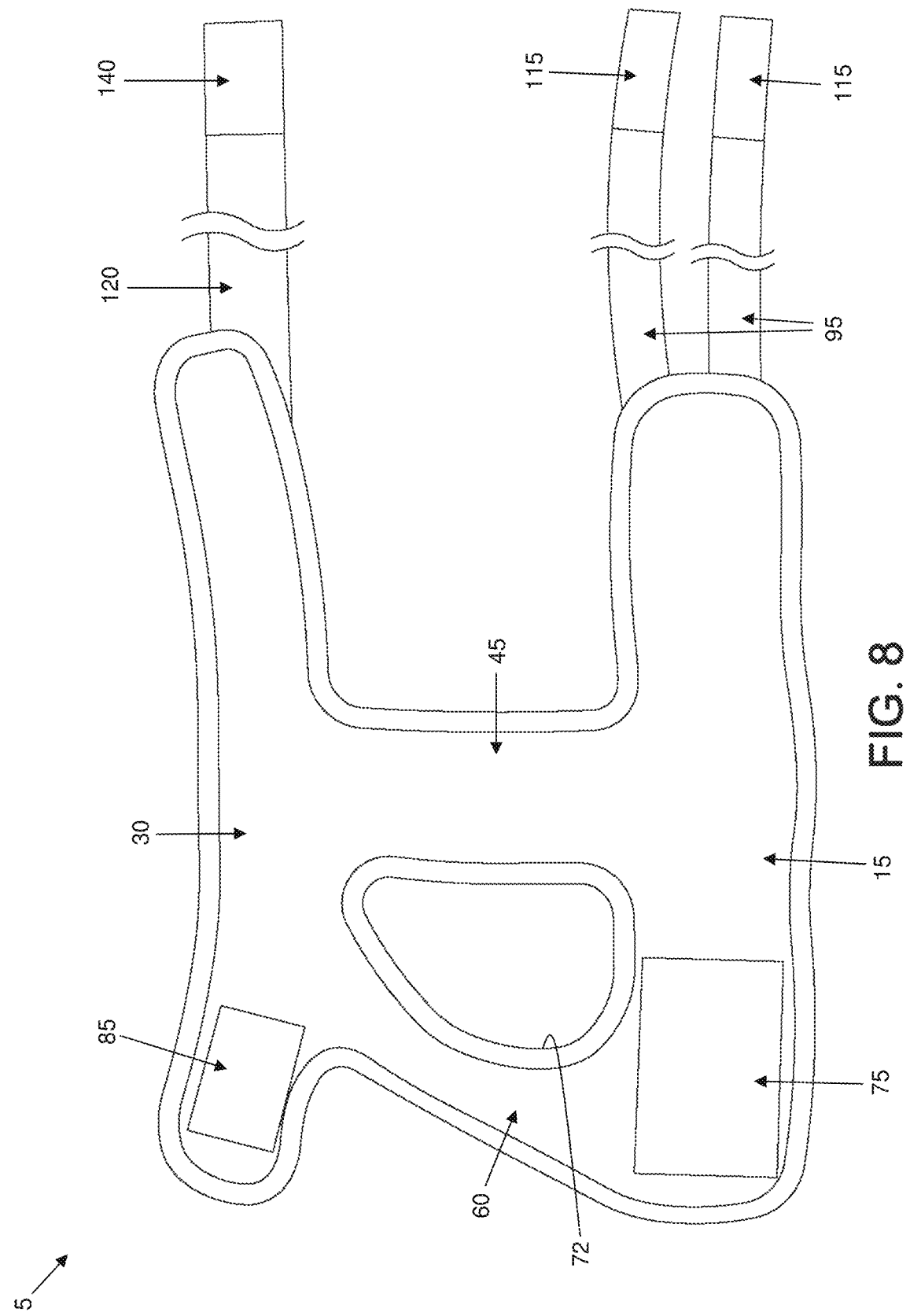
FIG. 8 is a schematic view showing the rear (posterior) side of the novel anatomical brace of the present invention, with the anatomical brace laid out flat on a surface.
Figure 9:
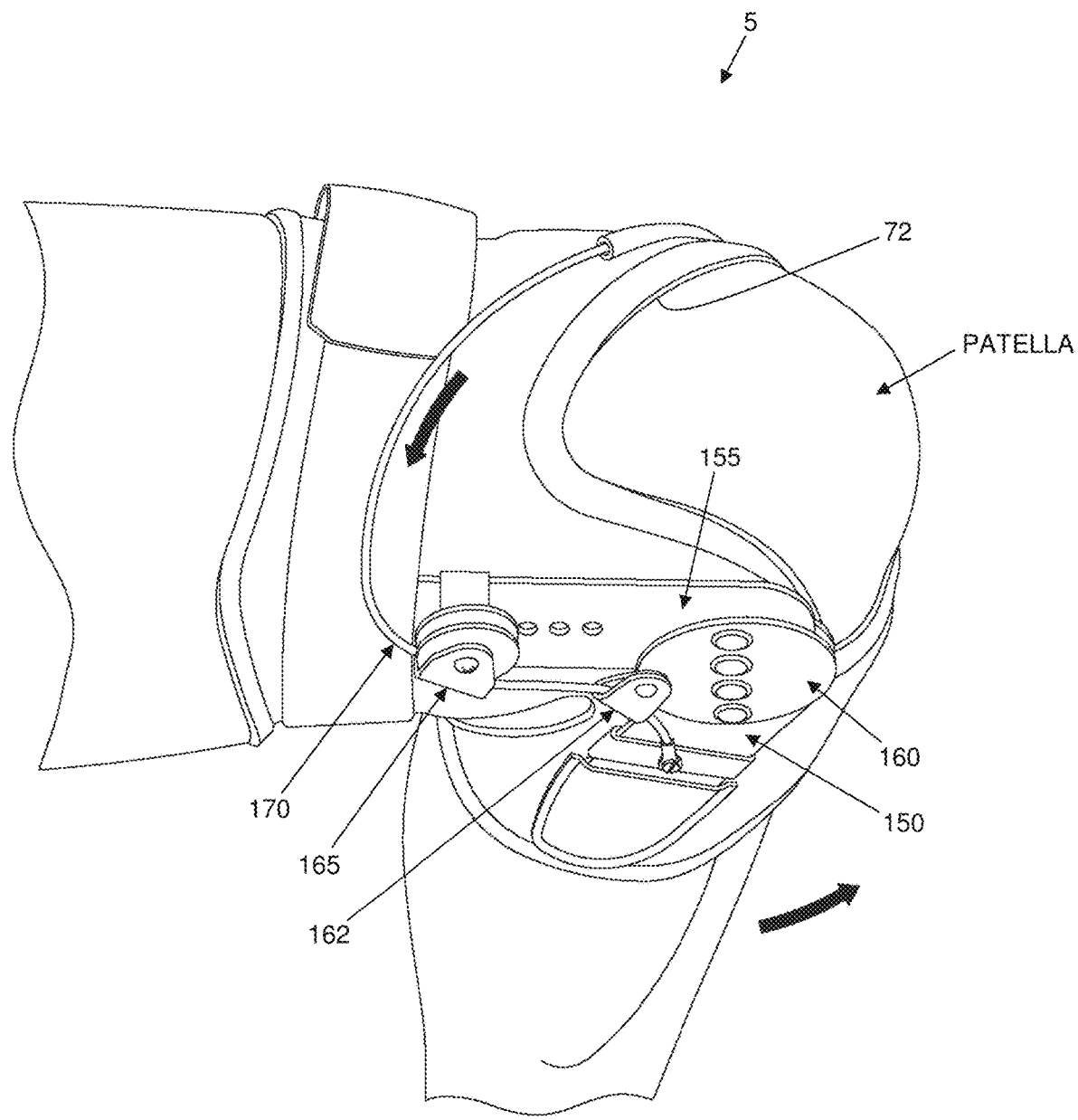
FIGS. 9-12 are schematic views showing operation of the novel anatomical brace as the knee moves from flexion to extension.
Figure 10:
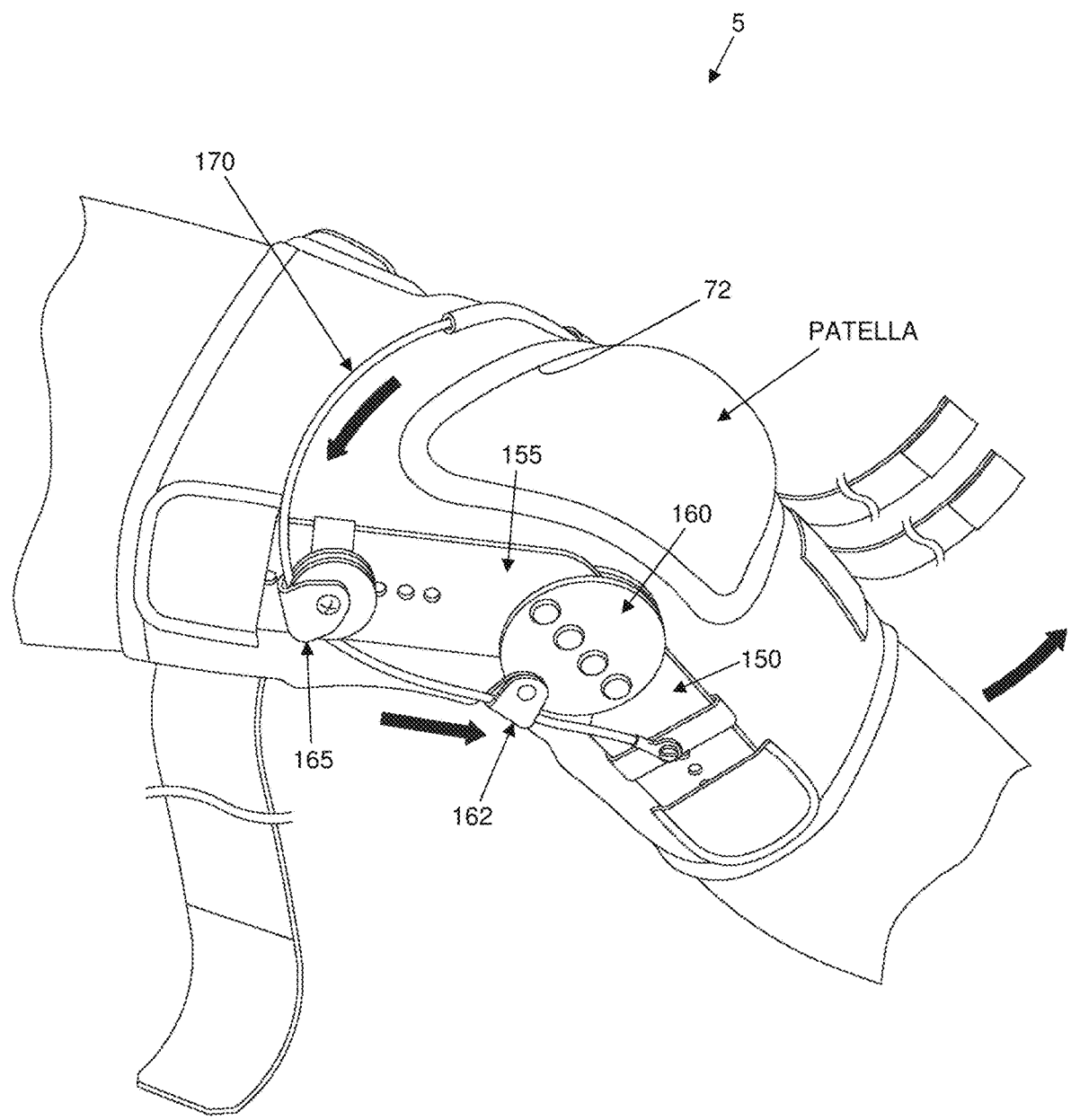
Figure 11:
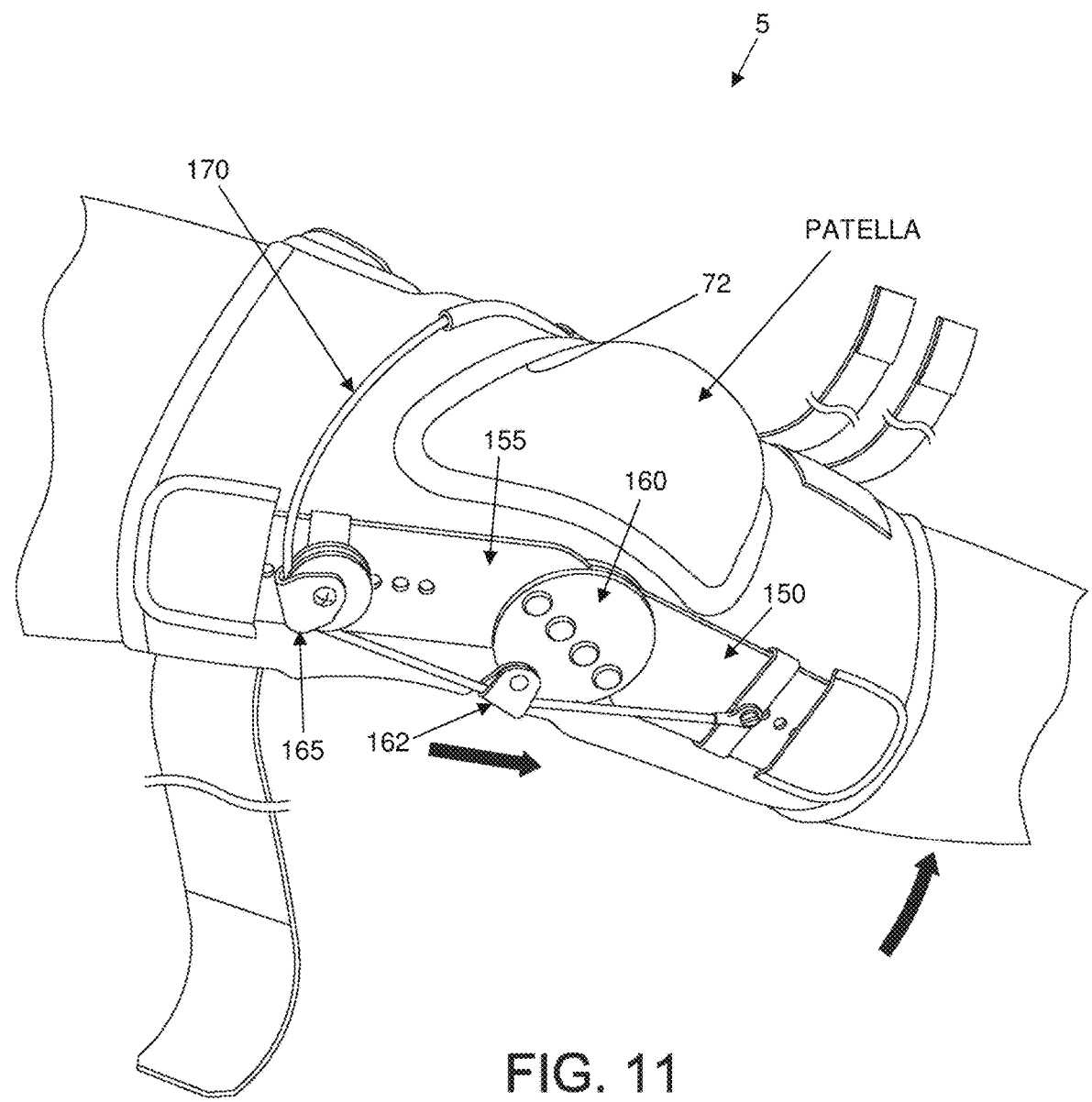
Figure 12:
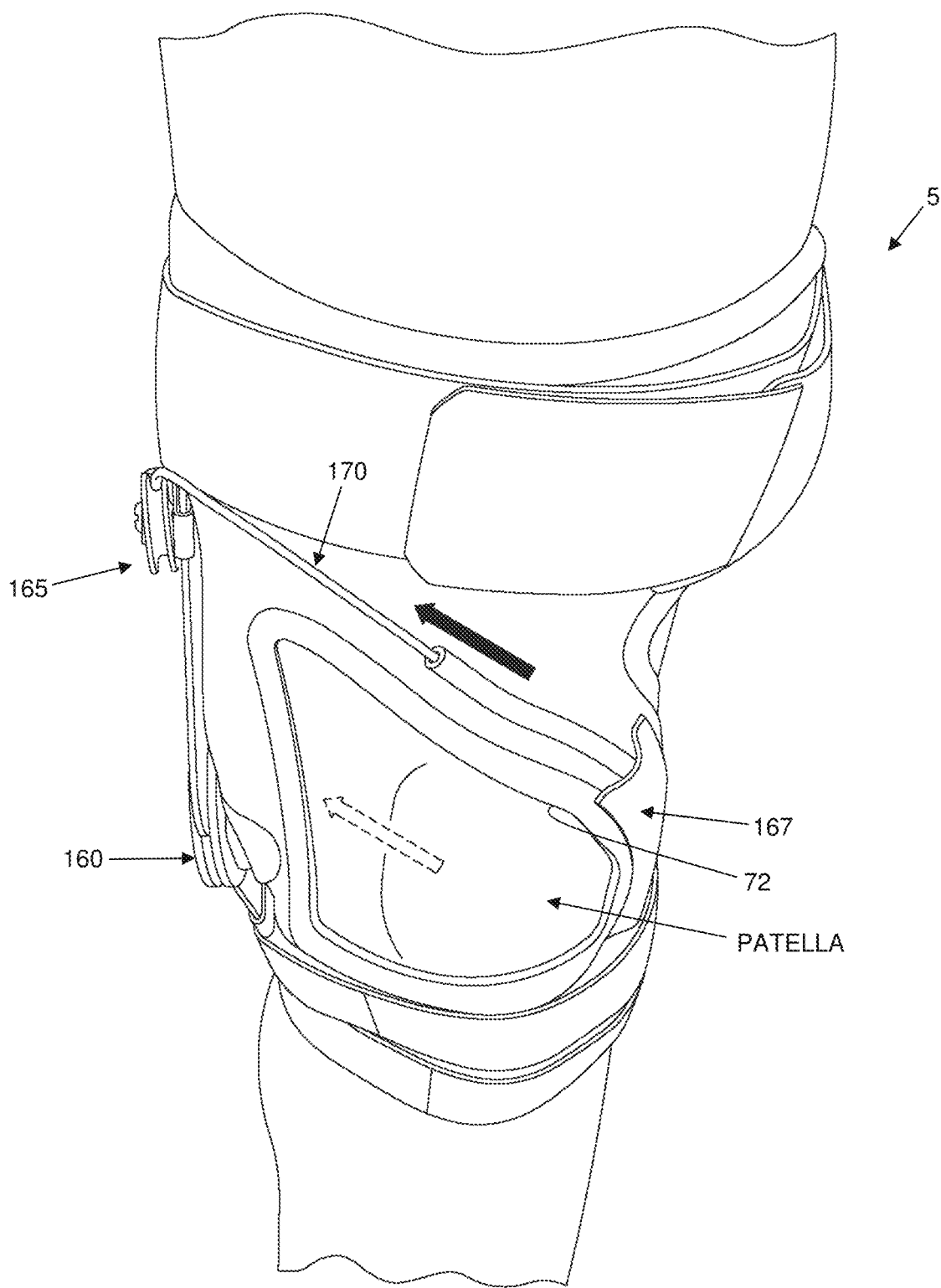

The present invention comprises the provision and use of a novel anatomical brace for dynamically stabilizing the patella during knee articulation so as to address patella tracking errors.

Among other things, the novel anatomical brace is configured to apply distal-to-proximal, as well as lateral-to-medial, forces (i.e., as distal-to-proximal/lateral-to-medial diagonal forces) to the patella as the knee moves from flexion to extension.

And the novel anatomical brace is configured to be relatively lightweight and non-intrusive, by eliminating the so-called "double hinge construction", and by avoiding the use of a substantial body of fabric on the posterior side of the knee which could impede full flexion of the knee (e.g., due to bunching in the back of the brace).

And the novel anatomical brace is configured to be more resistant to migration during use, by providing a more robust securement to the calf of the patient and by providing a more robust securement to the thigh of the patient.

And the novel anatomical brace is configured to relax the forces applied to the patella during knee flexion so that the novel anatomical brace is not "too tight" around the kneecap during knee flexion.

Construction of the Novel Anatomical Brace

Looking first at FIGS. 1-8, in one preferred form of the invention there is provided a novel anatomical brace 5 for dynamically stabilizing the patella during knee articulation so as to address patella tracking errors. Anatomical brace 5 generally comprises a brace body 10 comprising a distal band 15 having a first end 20 and a second end 25, a proximal band 30 having a first end 35 and a second end 40, a medial connector 45 having a distal end 50 and a proximal end 55, and a lateral connector 60 having a distal end 65 and a proximal end 70. Distal band 15, proximal band 30, medial connector 45 and lateral connector 60 together define a central opening 72 within brace body 10. Brace body 10 is flexible, and is preferably formed out of a flexible sheet material such as a woven fabric, a synthetic rubber, etc. In one preferred form of the invention, brace body 10 is formed out of neoprene or a neoprene blend.

One half 75 of a hook-and-mesh (e.g, Velcro®) fastener is fixed to the front (anterior) side of first end 20 of distal band 15 and the other half 80 of a hook-and-mesh (e.g, Velcro®) fastener is fixed to the rear (posterior) side of second end 25 of distal band 15, such that distal band 15 can be wrapped about the calf of a patient and secured in place. One half 85 of a hook-and-mesh (e.g., Velcro®) fastener is fixed to the front (anterior) side of first end 35 of proximal band 30 and the other half 90 of a hook-and-mesh (e.g., Velcro®) fastener is fixed to the rear (posterior) side of second end 40 of proximal band 30, such that proximal band 30 can be wrapped about the thigh of a patient and secured in place.

A pair of distal straps 95, each having a first end 100 and a second end 105, are secured to distal band 15 at their first ends 100. One half 110 of a hook-and-mesh (e.g, Velcro®) fastener is fixed to the front (anterior) side of each of first ends 100 of distal straps 95 and the other half 115 of a hook-and-mesh (e.g, Velcro®) fastener is fixed to the rear (posterior) side of each of second ends 105 of distal straps 95, such that distal straps 95 can be wrapped over distal band 15 and secured in place after distal band 15 has been secured to the calf of a patient.

A proximal strap 120, having a first end 125 and a second end 130, is secured to proximal band 30 at its first end 125. One half 135 of a hook-and-mesh (e.g., Velcro®) fastener is fixed to the front (anterior) side of first end 125 of proximal strap 120 and the other half 140 of a hook-and-mesh (e.g., Velcro®) fastener is fixed to the rear (posterior) side of second end 130 of proximal strap 120, such that proximal strap 120 can be wrapped over proximal band 30 and secured in place after proximal band 30 has been secured to the thigh of a patient.

Central opening 72 of brace body 10 is sized to receive the patella of a patient, as will hereinafter be discussed.

A hinge mechanism 145 is mounted over medial connector 45 and secured to distal band 15 and proximal band 30. More particularly, hinge mechanism 145 comprises a distal segment 150 and a proximal segment 155, with distal segment 150 being connected to proximal segment 155 at a pivot 160. Distal segment 150 of hinge mechanism 145 is secured to distal band 15 and proximal segment 155 of hinge mechanism 145 is secured to proximal band 30. Distal segment 150 of hinge mechanism 145, and proximal segment 155 of hinge mechanism 145, are each relatively stiff, and are preferably formed out of a lightweight metal, or a plastic, or a carbon fiber, etc. Pivot 160 of hinge mechanism 145 is relatively frictionless (i.e., it is easily articulated) and is preferably formed as an assembly comprising a central disc-shaped body to which both distal segment 150 and proximal segment 155 are pivotally attached. Alternatively, pivot 160 can comprise a simple "rivet pivot" or "screw pivot" of the sort well known in the art.

A first cable guide (e.g., a pivot guide) 162 is mounted to the portion of pivot 160 which faces posteriorly when anatomical brace 5 is secured to the knee of a patient (for purposes of the present disclosure, first cable guide 162 is sometimes hereinafter referred to as being mounted to "the posterior portion of pivot 160", and/or to "the posterior side of pivot 160", etc.).

A second cable guide (e.g., a guide pulley) 165 is adjustably mounted to proximal segment 155 of hinge mechanism 145. More particularly, second cable guide (e.g., guide pulley) 165 is mounted to proximal segment 155 of hinge mechanism 145 so that the distance between second cable guide (e.g., guide pulley) 165 and pivot 160 may be adjusted by the user. In one preferred form of the invention, second cable guide (e.g., guide pulley) 165 is adjustably mounted to proximal segment 155 of hinge mechanism 145, e.g., using a screw and a plurality of holes.

A third cable guide (e.g., a brace tunnel) 167 is formed on lateral connector 60. Where third cable guide 167 comprises a brace tunnel, the brace tunnel may be formed out of the same material as brace body 10, or the brace tunnel may be formed out of a different material than brace body 10.

A cable 170 extends between distal segment 150 of hinge mechanism 145 and a distal lateral portion of brace body 10 of anatomical brace 5. More particularly, cable 170 comprises a first end 182 which is adjustably secured to distal segment 150 of hinge 145, and a second end 183 which is adjustably secured to a lateral portion of distal band 15, with the intermediate portion of cable 170 extending proximally along distal segment 150 of hinge mechanism 150, through first cable guide (e.g., pivot guide) 162, proximally along proximal segment 155 of hinge mechanism 150, through second cable guide (e.g., guide pulley) 165, laterally along proximal band 30, distally along lateral connector 60, and then through third cable guide (e.g., brace tunnel) 167.

Note that with this cable pathway, first end 182 of cable 170 passes through first cable guide (e.g., pivot guide) 162, which is positioned on the posterior side of pivot 160 so as to keep first end 182 of cable 170 toward the posterior side of pivot 160. By virtue of this construction, and as will hereinafter be discussed in further detail, cable 170 is able to release tension when the knee flexes and increase tension when the knee extends. This is a significant improvement in the art. Thus it will be seen that the present invention provides a hinged knee brace (i.e., a patellofemoral knee brace) with a cable system where the cable passes along the length of the hinge and posteriorly to the hinge pivot. This unique design allows for tightening of the cable (therefore resulting in the application of pressure to the kneecap) during knee extension and loosening of the cable (therefore resulting in releasing pressure from the kneecap) during flexion.

And note that with this cable pathway, second end 183 of cable 170 passes through third cable guide (e.g., brace tunnel) 167 positioned on lateral connector 60 so as to stabilize second end 183 of cable 170 laterally of the patella, and second end 183 of cable 170 is secured to a lateral portion of distal band 15. By virtue of this construction, cable 170 is able to apply lateral-to-medial, and distal-to-proximal, forces (i.e., as distal-to-proximal/lateral-to-medial diagonal forces) to the patella as the knee moves from flexion to extension.

It should be appreciated that first end 182 of cable 170 is adjustably mounted to distal segment 150 of hinge mechanism 145 such that the position of first end 182 of cable 170 can be adjusted relative to distal segment 150 of hinge mechanism 145, whereby to change the angle, direction and/or tension of cable 170, in order to accommodate the patient's anatomy. In one preferred form of the invention, first end 182 of cable 170 is adjustably mounted to distal segment 150 of hinge mechanism 145 using a screw and a plurality of holes.

It should also be appreciated that second end 183 of cable 170 is adjustably mounted to distal band 15 of brace body 10 such that the position of second end 183 of cable 170 can be adjusted relative to distal band 15 of brace body 10, whereby to change the angle, direction and/or tension of cable 170, in order to accommodate the patient's anatomy. In one preferred form of the invention, second end 183 of cable 170 is adjustably mounted to distal band 15 using a hook-and-mesh (e.g., Velcro®) fastener. By way of example but not limitation, one half 184 of a hook-and-mesh (e.g., Velcro®) fastener is fixed to second end 183 of cable 170 and the other half of a hook-and-mesh (e.g., Velcro®) fastener is provided by the element 75 previously described.

And it should be appreciated that second cable guide (e.g., guide pulley) 165 is adjustably mounted to proximal segment 155 of hinge mechanism 145 such that the position of second cable guide (e.g., guide pulley) 165 on proximal segment 155 of hinge mechanism 145 can be adjusted, whereby to change the angle, direction and/or tension of cable 170, in order to accommodate the patient's anatomy.

In one preferred form of the invention, first end 182 of cable 170 is formed out of a relatively inelastic material such as stainless steel and second end 183 of cable 170 is formed out of an elastomeric material (e.g., rubber, a rubber substitute, an elastic weave, etc.). As a result of this construction, when cable 170 is tensioned, first end 182 of cable 170 is substantially unstretchable while second end 175 of cable 170 can elongate to some (i.e., a limited) extent.

Note that forming second end 183 of cable 170 out of an elastomeric material has several significant advantages. First, it is convenient for the healthcare professional during fitting of anatomical brace 5, since it minimizes the need for cable sizing and eliminates concerns about excessive or inadequate cable lengths. Second, it eliminates concerns about cable bunching when the knee is in flexion (i.e., when the knee is bent), since the elastomeric nature of the cable takes up excess cable length when tension on the cable is relaxed. Third, the elastomeric nature of the cable is able to accommodate the patient's anatomy during extension (i.e., knee straightening), and eliminates the concern that the limit of the cable will be reached before the leg is in full extension. Of course, it will also be appreciated that while second end 183 of cable 170 is preferably elastic to some (i.e., a limited) extent, it is not so elastic as to prevent cable 170 and brace body 10 from applying forces to the patella during flexion of the knee. And fourth, during knee extension, the elastomeric nature of second end 183 of the tensioned cable 170 pulls the tibia towards the femur, whereby to provide (through the patella tendon) distal-to-proximal forces on the patella (which reduces the load on the patella tendon, thereby making anatomical brace 5 useful for patients with patella tendonitis).

Use of the Novel Anatomical Brace

In use, and still looking now at FIGS. 1-8, anatomical brace 5 is first secured to the patient by positioning brace body 10 over the knee so that central opening 72 of brace body 10 receives the patella of the patient and makes a relatively close fit about the distal and lateral portions of the patella, placing medial connector 45 over the medial portion of the knee, and placing lateral connector 60 over the lateral portion of the knee; and by fitting distal band 15 about the calf of the patient and making it fast with hook-and-mesh (e.g, Velcro®) fastener 75, 80, and fitting proximal band 30 about the thigh of the patient and making it fast with hook-and-mesh (e.g., Velcro®) fastener 85, 90. Then distal straps 95 are tightened about distal band 15 using hook-and-mesh (e.g., Velcro®) fasteners 110, 115, and proximal strap 120 is tightened about proximal band 30 using hook-and-mesh (e.g, Velcro®) fastener 135, 140.

Note that by positioning brace body 10 so that central opening 72 of brace body 10 receives the patella of the patient, brace body 10 and cable 170 of anatomical brace 5 will surround the patella of the patient.

Note also that by securing distal straps 95 over distal band 15, a more secure yet comfortable attachment can be made to the calf of the patient, and by securing proximal strap 120 over proximal band 30, a more secure yet comfortable attachment can be made to the thigh of the patient.

Note further that when anatomical brace 5 is positioned in this manner about the knee of the patient, hinge mechanism 145 will extend along the medial portion of the knee, and the rear of the knee is left substantially uncovered by anatomical brace 5.

And note also that no hinge mechanism is disposed along the lateral portion of the knee.

Next, cable 170 has its first end 182 adjustably secured to distal segment 150 of hinge mechanism 145. Then, with the knee close to (but not at) full extension (i.e., with the knee nearly straightened), cable 170 is routed proximally along distal segment 150 of hinge mechanism, through first cable guide (e.g., pivot guide) 162, proximally along proximal segment 155 of hinge mechanism 150, through second cable guide (e.g., guide pulley) 165, laterally along proximal band 30, distally along lateral connector 60, through third cable guide (e.g., brace tunnel) 167 and then down to a distal lateral portion of brace body 10 of anatomical brace 5 (e.g. to hook-and-fastener element 75), where second end 183 of cable 170 is adjustably secured in place.

Note that when cable 170 is routed in this manner, the cable passes posterior to pivot 160 and alongside, and substantially engages, the lateral portions of the patella, and terminates distal to the patella.

As a result, when the knee thereafter moves to full extension, cable 170 is tensioned, whereby to apply a distal-to-proximal, as well as lateral-to-medial, force (i.e., as distal-to-proximal/lateral-to-medial diagonal forces) on the patella; and when the knee thereafter moves to flexion, cable 170 is relaxed, so that the forces applied to the patella by the cable are also relaxed.

More particularly, when the knee moves to full extension, cable 170 is tensioned, whereby to pull brace body 10 of anatomical brace 5 proximally and medially (i.e., in a proximal/medial diagonal direction). This proximal/medial force is applied to (i) the patella of the patient via brace body 10 (inasmuch as central opening 72 of brace body 10 receives the patella of the patient and makes a relatively close fit about the distal and lateral portions of the patella), and (ii) the tibia of the patient (inasmuch as distal band 15 or brace body 10 is secured to the upper calf of the patient, and hence the tibia of the patient, and the second end 183 of cable 170 is anchored to distal band 15), which force is in turn transferred to the patella via the patella tendon. See FIGS. 9-12.

Figure 13:
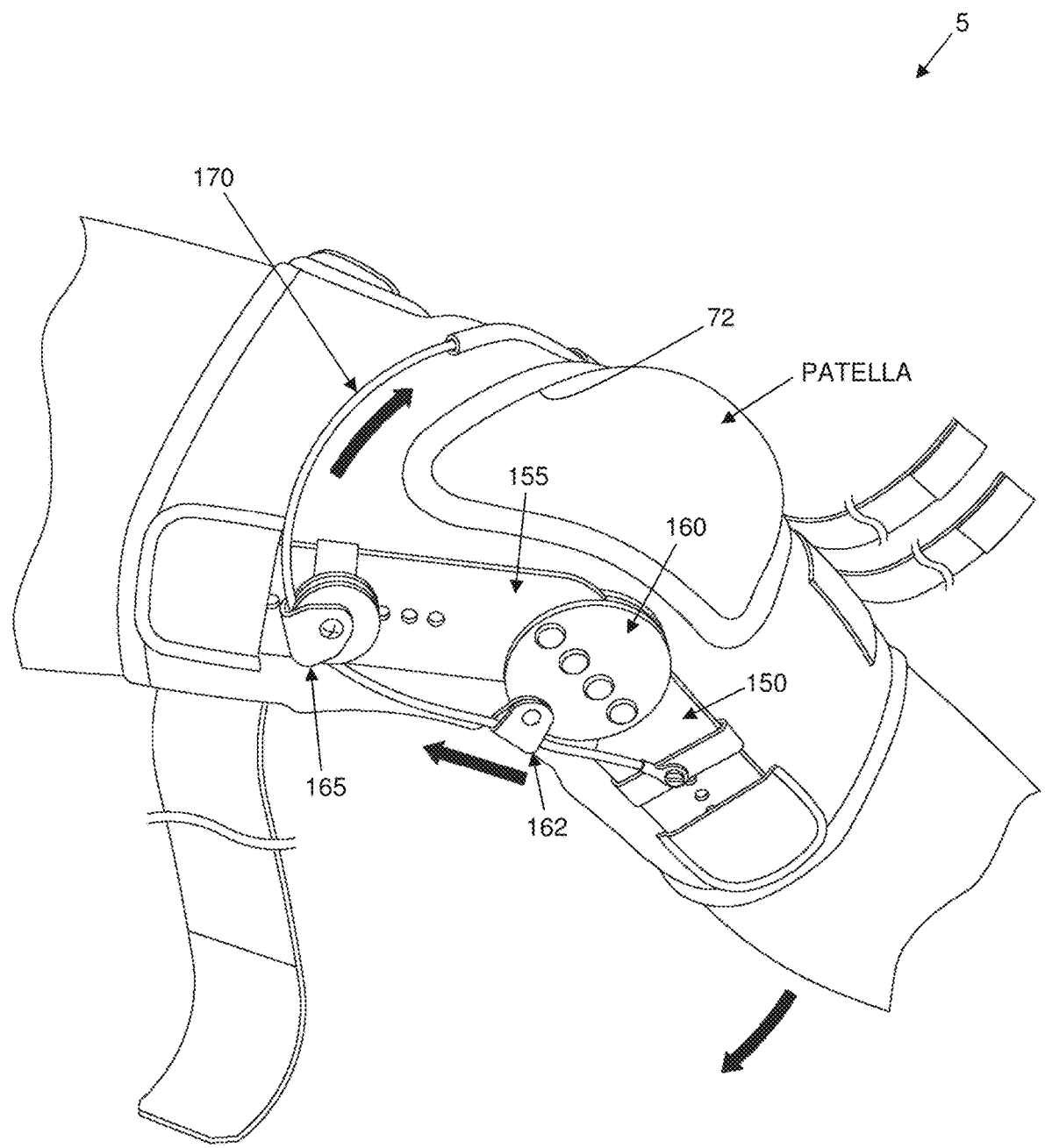
FIGS. 13 and 14 are schematic views showing operation of the novel anatomical brace as the knee moves from extension to flexion.
Figure 14:
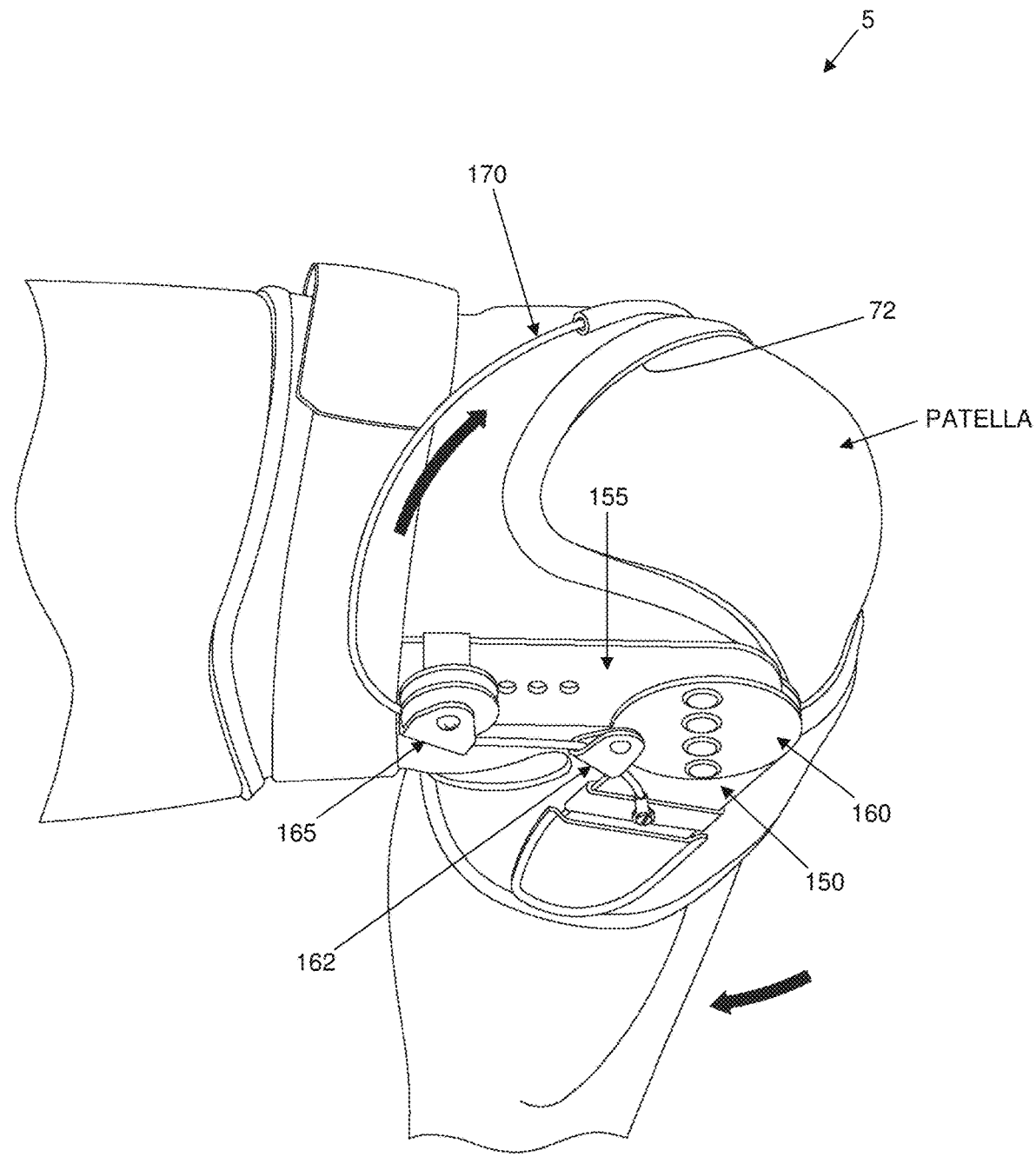

Conversely, when the knee moves to full flexion, cable 170 is relaxed, so that the proximal/medial diagonal force on brace body 10 (and hence the patella of the patient) is released. See FIGS. 13 and 14.

Thus it will be seen that, on account of the foregoing construction, when the knee articulates from flexion to extension (see FIGS. 9-12), anatomical brace 5 applies distal-to-proximal, as well as lateral-to-medial, forces (i.e., as distal-to-proximal/lateral-to-medial diagonal forces) on the patella, whereby to correct for patella tracking errors, and when the knee articulates from extension to flexion (see FIGS. 13 and 14), anatomical brace 5 relaxes the forces applied to the patella.

This is a significant improvement in the art.

Among other things, the use of a guided cable system that allows the anatomical brace to engage the patella with distal-to-proximal, as well as lateral-to-medial, forces (i.e., as distal-to-proximal/lateral-to-medial diagonal forces) during knee extension, and relax those forces during knee flexion, is a unique feature not found in the prior art and which is highly advantageous over the anatomical braces of the prior art. This is made possible by the use of the unique guided cable system of the present invention, where the cable passes along the length of the hinge mechanism and posteriorly to the hinge pivot.

Among other things, it should also be noted that by providing cable 170 with an elastic second end 183, cable 170 can stretch (to some extent) when the cable is tensioned during knee extension (i.e., during knee straightening), and cable 170 can contract (to some extent) when the cable is relaxed during knee flexion (i.e., during knee bending).

And it should be noted that, forming second end 183 of cable 170 out of an elastomeric material (i) provides increased convenience for the healthcare professional during fitting of anatomical brace 5, since it minimizes the need for cable sizing and eliminates concerns about excessive or inadequate cable lengths; (ii) eliminates concerns about cable bunching when the knee is in flexion (i.e., when the knee is bent), since the elastomeric nature of the cable takes up excess cable length when tension on the cable is relaxed; (iii) accommodates the patient's anatomy during extension (i.e., knee straightening), and eliminates the concern that the limit of the cable will be reached before the leg is in full extension; (of course, it will also be appreciated that while second end 183 of cable 170 is preferably elastic to some extent, it is not so elastic as to prevent cable 170 and brace body 10 from applying forces to the patella during flexion of the knee); and (iv) during knee extension, the elastomeric nature of second end 183 of the tensioned cable 170 pulls the tibia toward the femur, whereby to provide (through the patella tendon) distal-to-proximal forces on the patella (which reduces the load on the patella tendon, thereby making anatomical brace 5 useful for patients with patella tendonitis).

These features are also significant improvements in the art.

Significantly, anatomical brace 5 is relatively lightweight and non-intrusive, since it utilizes a single-hinge construction and avoids a so-called "double hinge construction", and avoids the use of a substantial body of fabric on the posterior side of the knee which could impede full flexion of the knee (e.g., due to bunching in the back of the brace). Thus it will be seen that the present invention provides a light weight and low profile brace that, among other things, prevents bunching in the back of the brace and tightness when the knee is bent.

And anatomical brace 5 is more resistant to migration during use, by providing a more robust securement to the calf of the patient and by providing a more robust securement to the thigh of the patient.

And anatomical brace 5 is configured to relax the forces applied to the patella during knee flexion so that anatomical brace 5 is not "too tight" around the kneecap during knee flexion.

Figure 15:
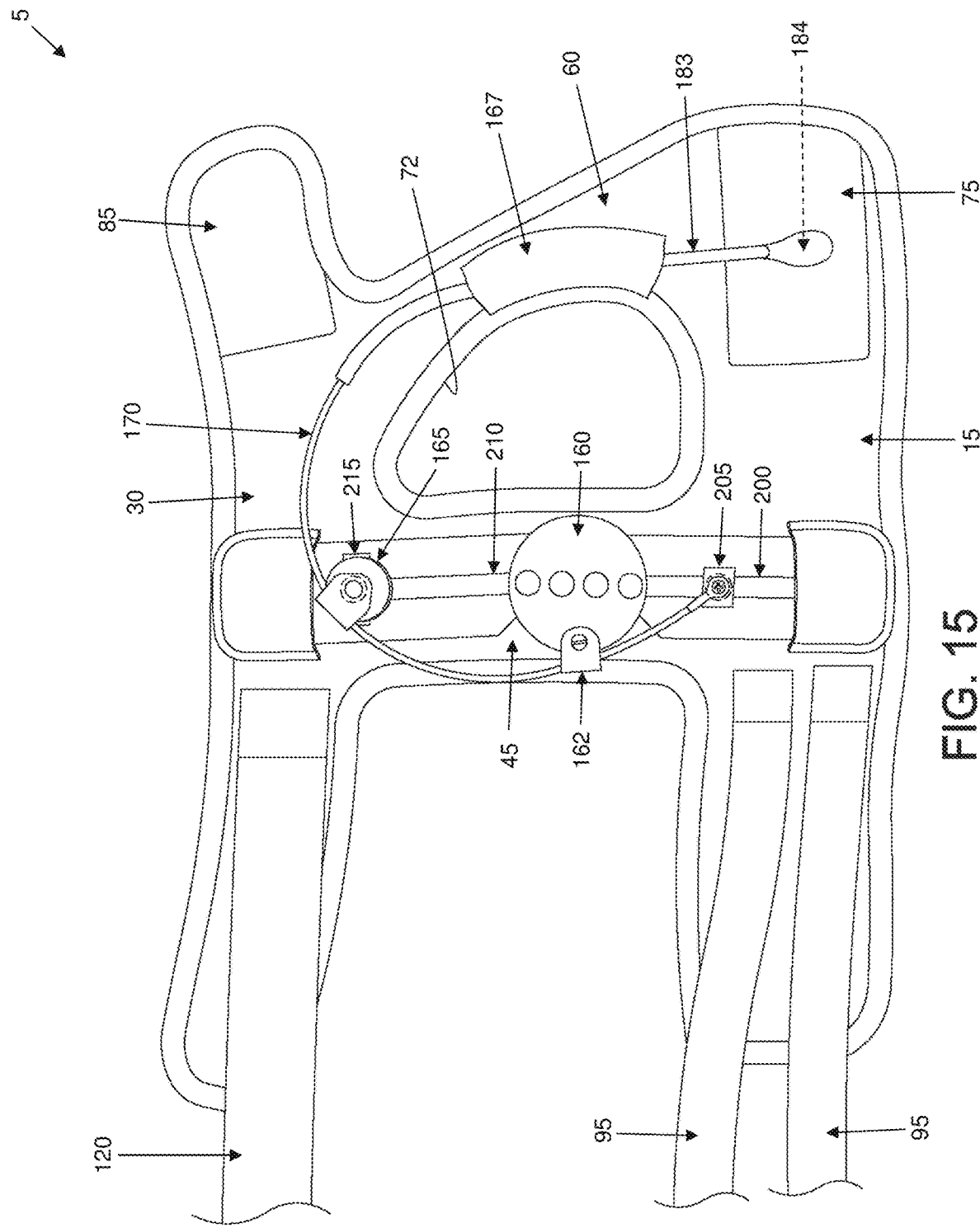
FIG. 15 is a schematic view showing another form of the novel anatomical brace of the present invention.

In the foregoing disclosure, it was noted that first end 182 of cable 170 is adjustably mounted to distal segment 150 of hinge mechanism 145 such that the position of first end 182 of cable 170 can be adjusted relative to distal segment 150 of hinge mechanism 145, whereby to change the angle, direction and/or tension of cable 170, in order to accommodate the patient's anatomy; and it was noted that in one preferred form of the invention, first end 182 of cable 170 is adjustably mounted to distal segment 150 of hinge mechanism 145 using a screw and a plurality of holes. However, it will be apparent to those skilled in the art that many other mounting mechanisms may be utilized if desired. By way of example but not limitation, and looking now at FIG. 15, first end 182 of cable 170 may adjustably mounted to distal segment 150 of hinge mechanism 145 by providing a rail 200 on distal segment 150 of hinge mechanism 145, and by mounting first end 182 of cable 170 to a rider 205 which is slidably mounted to rail 200, with a fixation element (e.g., a set screw, not shown) being used to lock rider 205 in place at a desired position along rail 200.

And in the foregoing disclosure, it was noted that second cable guide (e.g., guide pulley) 165 is adjustably mounted to proximal segment 155 of hinge mechanism 145 such that the position of second cable guide (e.g., guide pulley) 165 can be adjusted relative to proximal segment 155 of hinge mechanism 145, whereby to change the angle, direction and/or tension of cable 170, in order to accommodate the patient's anatomy; and it was noted that in one preferred form of the invention, second cable guide (e.g., guide pulley) 165 is adjustably mounted to proximal segment 155 of hinge mechanism 145 using a screw and a plurality of holes. However, it will be apparent to those skilled in the art that many other mounting mechanisms may be utilized if desired. By way of example but not limitation, and looking now at FIG. 15, second cable guide (e.g., guide pulley) 165 may adjustably mounted to proximal segment 155 of hinge mechanism 145 by providing a rail 210 on proximal segment 155 of hinge mechanism 145, and by mounting second cable guide (e.g., guide pulley) 165 to a rider 215 which is slidably mounted to rail 210, with a fixation element (e.g., a set screw, not shown) being used to lock rider 215 in place at a desired position along rail 210.

Figure 16:
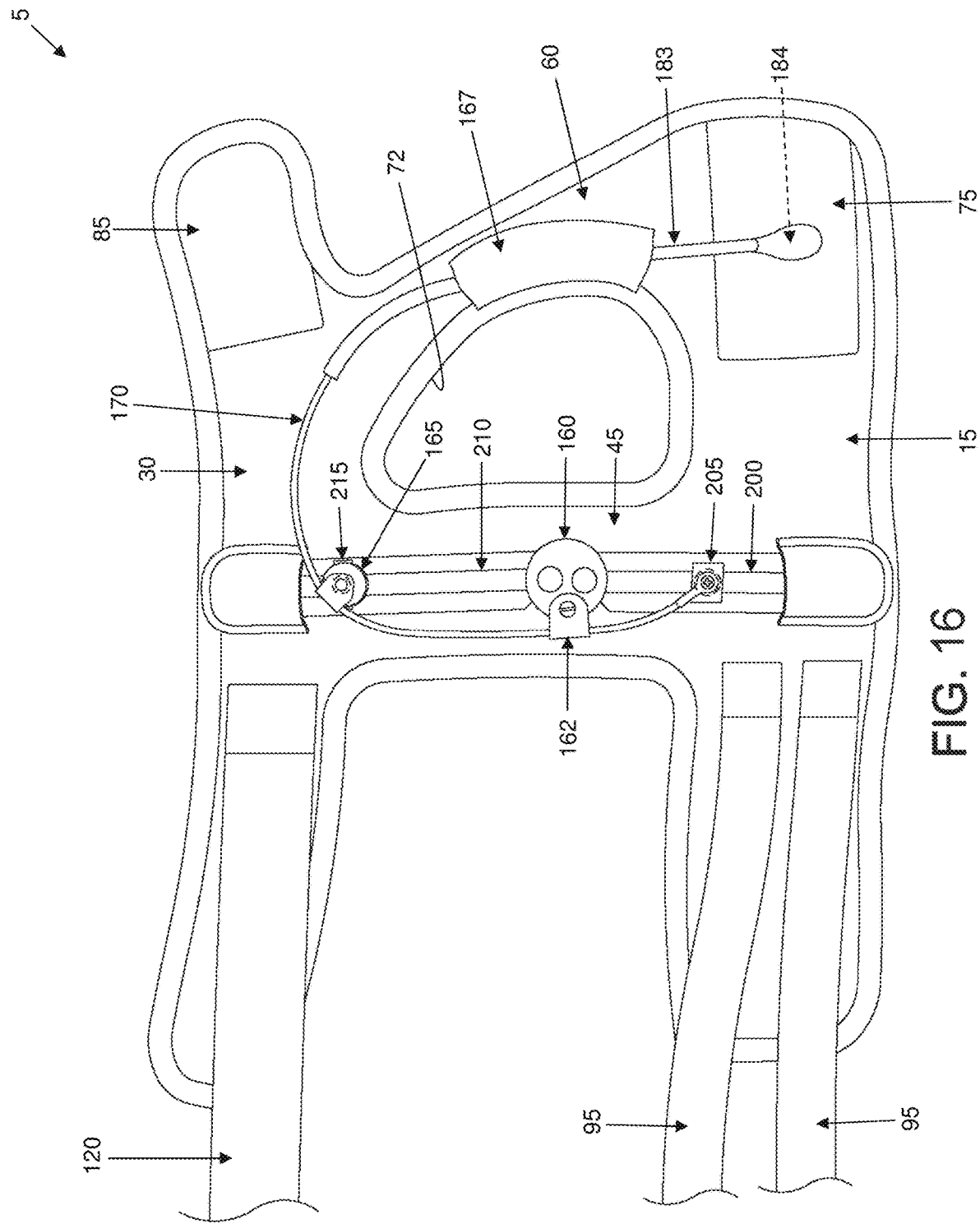
FIG. 16 is a schematic view showing still another form of the novel anatomical brace of the present invention.

FIG. 16 shows another form of the novel anatomical brace of the present invention. This form of the invention is generally similar to the construction shown in FIG. 15, except that various components of the hinge mechanism are formed with a lighter weight construction.

And in the foregoing disclosure it was noted that second end 183 of cable 170 is adjustably mounted to distal band 15 of brace body 10 such that the position of second end 183 of cable 170 can be adjusted relative to distal band 15 of brace body 10, whereby to change the angle, direction and/or tension of cable 170, in order to accommodate the patient's anatomy; and it was noted that in one preferred form of the invention, second end 183 of cable 170 is adjustably mounted to distal band 15 of brace body 10 using a hook-and-mesh (e.g. Velcro®) fastener. However, it will be apparent to those skilled in the art that many other mounting mechanisms (e.g., snap fasteners, cable clamps, cable tie-downs, etc.) may be used to adjustably mount second end 183 of cable 170 to distal band 15 of brace body 10.

In the foregoing disclosure, it is noted that first cable guide 162 may be a pivot guide, second cable guide 165 may be a guide pulley, and third cable guide 167 may be a brace tunnel; however, it should also be appreciated that other elements (e.g., rings, eyelets, tubes, etc.) may be used to form first cable guide 162, second cable guide 165 and/or third cable guide 167 (i.e., essentially any structure capable of guiding cable 170 in a manner consistent with the present invention).

Figure 17:
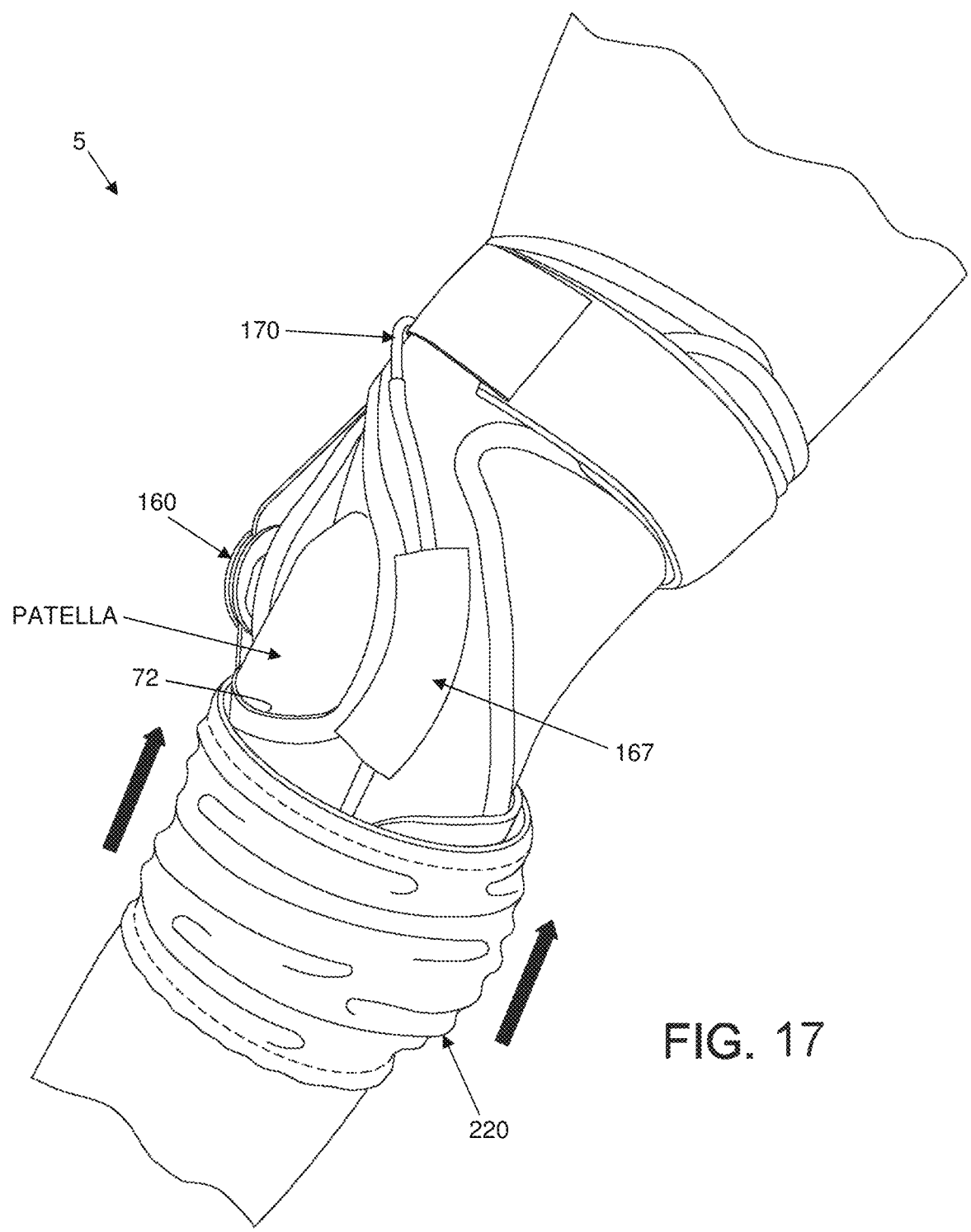
FIG. 17 is a schematic view showing one form of a cover which may be positioned over the novel anatomical brace during use.

In addition to the foregoing, it will also be appreciated that it may be desirable to provide a covering for novel anatomical brace 5 so as to shield the operative elements of the anatomical brace from inadvertent contact during use, e.g., to shield hinge mechanism 145, cable 170, first cable guide (e.g., guide pulley) 162, second cable guide (e.g., guide pulley) 165, third cable guide (e.g., brace tunnel) 167, etc. from inadvertent contact during use. To this end, and looking now at FIG. 17, an elastic sleeve 220 may be provided for selectively covering novel anatomical brace 5, with the elastic sleeve 220 being pulled up over the anatomical brace during use. Alternatively, an overlying covering or panel may be permanently (or temporarily) attached to anatomical brace 5 (e.g., to portions of brace body 10), with the covering or panel able to be laid open (e.g., folded back) when it is necessary to access the operative elements of the anatomical brace (e.g., to adjust the disposition of cable 170) and the covering or panel being closable (e.g., laid back over the operative elements and secured in place) when the anatomical brace is in use.

Modifications

It is to be understood that the present invention is by no means limited to the particular constructions herein disclosed and/or shown in the drawings, but also comprises any modifications or equivalents within the scope of the invention.

What is claimed is:

1. An anatomical brace for dynamically stabilizing the patella of a patient during knee articulation so as to address patella tracking error, the anatomical brace comprising:
    a brace body for disposition about the knee of the patient, the brace body comprising a distal portion for securement about the calf of the patient, a proximal portion for securement about the thigh of the patient, and an intermediate portion for receiving the patella of the patient;
    a hinge mechanism for disposition on the medial side of the knee of the patient, the hinge mechanism comprising a distal segment, a proximal segment and a pivot for pivotally connecting the distal segment and the proximal segment, the distal segment of the hinge mechanism being connected to the distal portion of the brace body and the proximal segment of the hinge mechanism being connected to the proximal portion of the brace body; and
    a tensioner having a first end and a second end, the first end of the tensioner being secured to the hinge mechanism so that the first end of the tensioner moves in conjunction with the distal segment of the hinge mechanism, the tensioner extending posteriorly of the pivot and then proximally along the proximal segment of the hinge mechanism and then laterally across the brace body superior to the intermediate portion of the brace body which is configured to receive the patella of the patient and then distally along the intermediate portion of the brace body which is configured to receive the patella of the patient, and the second end of the tensioner being secured to the distal portion of the brace body;

the anatomical brace being configured such that, when the anatomical brace is mounted to the knee of the patient so that the distal portion of the brace body is secured to the calf of the patient, the proximal portion of the brace body is secured to the thigh of the patient and the intermediate portion of the brace body receives the patella of the patient, with the hinge mechanism being located on the medial side of the knee, and when the knee thereafter moves to full extension, the tensioner is tensioned, such that the intermediate portion of the brace body applies (i) a lateral-to-medial force to the patella of the patient, and (ii) a distal-to-proximal force to the patella of the patient, and when the knee thereafter moves to full flexion, the tensioner is relaxed, so as to relax (i) the lateral-to-medial force applied to the patella of the patient and (ii) the distal-to-proximal force applied to the patella of the patient.

2. The anatomical brace of claim 1:
wherein the distal portion of the brace body comprises distal band having a first end, a second end and a fastener for securing together said first end of said distal band and said second end of said distal band;
wherein the proximal portion of the brace body comprises a proximal band having a first end, a second end and a fastener for securing together said first end of said proximal band and said second end of said proximal band;
wherein the intermediate portion of the brace body comprises (i) a medial connector having a distal end and a proximal end, said distal end of said medial connector being connected to said distal band and said proximal end of said medial connector being connected to said proximal band, (ii) a lateral connector having a distal end and a proximal end, said distal end of said lateral connector being connected to said distal band and said proximal end of said lateral connector being connected to said proximal band;
wherein said distal band, said proximal band, said medial connector and said lateral connector together define a central opening sized to receive the patella of a patient;
wherein said distal segment of said hinge mechanism is connected to said distal band and said proximal segment of said hinge mechanism is connected to said proximal band;
wherein the anatomical brace further comprises:
a first cable guide mounted to a posterior portion of said pivot;
a second cable guide mounted to said proximal segment of said hinge mechanism;
a third cable guide secured to said lateral connector;
wherein said tensioner is routed proximally along said distal segment of said hinge mechanism, through said first cable guide, proximally along said proximal segment of said hinge mechanism, through said second cable guide, laterally along said proximal band, distally along said lateral connector and through said third cable guide.

3. The anatomical brace according to claim 2 wherein said fastener for securing together said first end of said distal band and said second end of said distal band comprises a hook-and-mesh fastener.

4. The anatomical brace according to claim 2 wherein said fastener for securing together said first end of said proximal band and said second end of said proximal band comprises a hook-and-mesh fastener.

5. The anatomical brace according to claim 2 wherein said first cable guide comprises one from the group consisting of a pivot guide, a guide pulley, a tunnel, a ring, an eyelet and a tube.

6. The anatomical brace according to claim 2 wherein said second cable guide is adjustably mounted to said proximal segment of said hinge mechanism.

7. The anatomical brace according to claim 2 wherein said second cable guide comprises one from the group consisting of a pivot guide, a guide pulley, a tunnel, a ring, an eyelet and a tube.

8. The anatomical brace according to claim 2 wherein said third cable guide comprises one from the group consisting of a pivot guide, a guide pulley, a tunnel, a ring, an eyelet and a tube.

9. The anatomical brace according to claim 1 wherein the tensioner comprises a cable and a connector attached to the cable, and further wherein the cable comprises the first end of the tensioner and the connector comprises the second end of the tensioner.

10. The anatomical brace according to claim 9 wherein the cable comprises a metallic or plastic material and the connector comprises a non-metallic material.

11. The anatomical brace according to claim 9 wherein the connector has a variable length.

12. The anatomical brace according to claim 9 wherein the connector comprises an elastomer.

13. The anatomical brace according to claim 1 wherein said brace body comprises a flexible sheet material.

14. The anatomical brace according to claim 13 wherein said flexible sheet material comprises at least one from the group consisting of a woven fabric and a synthetic rubber.

15. The anatomical brace according to claim 14 wherein said flexible sheet material comprises neoprene.

16. The anatomical brace according to claim 1 wherein said anatomical brace is configured so that, when said anatomical brace is mounted to the knee of a patient, and when the knee of the patient thereafter moves to full flexion, said anatomical brace does not bunch in the back of said anatomical brace and cause tightness in the back of the knee of the patient.

17. The anatomical brace according to claim 1 wherein said pivot of said hinge mechanism comprises a central disk-shaped body to which said distal segment of said hinge mechanism and said proximal segment of said hinge mechanism are pivotally attached.

18. The anatomical brace according to claim 1 wherein said pivot of said hinge mechanism comprises one from the group consisting of a rivet pivot and a screw pivot.

19. The anatomical brace according to claim 1 wherein said first end of said tensioner is elastic and said second end of said tensioner is substantially inelastic.

20. The anatomical brace according to claim 1 wherein said first end of said tensioner is adjustably mounted to said distal segment of said hinge mechanism.

21. The anatomical brace according to claim 1 wherein said second end of said tensioner is adjustably mounted to the distal portion of the brace body.

22. An anatomical brace for dynamically stabilizing the patella of a patient during knee articulation so as to address patella tracking error, the anatomical brace comprising:
a brace body for disposition about the knee of the patient,
the brace body comprising a distal portion for securement about the calf of the patient, a proximal portion for securement about the thigh of the patient, and an intermediate portion for receiving the patella of the patient;

a hinge mechanism for disposition on the medial side of the knee of the patient, the hinge mechanism comprising a distal segment, a proximal segment and a pivot for pivotally connecting the distal segment and the proximal segment, the distal segment of the hinge mechanism being connected to the distal portion of the brace body and the proximal segment of the hinge mechanism being connected to the proximal portion of the brace body; and a tensioner mounted to the hinge mechanism, passing posterior to the pivot of the hinge mechanism, and mounted to the brace body, such that (i) during knee extension, the tensioner and the brace body are configured to impart a medially-directed force on the patella, and (ii) during knee flexion, that medially-directed force is relaxed.

23. The anatomical brace according to claim 22 wherein the tensioner comprises a cable and a connector attached to the cable, and further wherein the cable comprises the first end of the tensioner and the connector comprises the second end of the tensioner.

24. The anatomical brace according to claim 23 wherein the cable comprises a metallic or plastic material and the connector comprises a non-metallic material.

25. The anatomical brace according to claim 23 wherein the connector has a variable length.

26. The anatomical brace according to claim 23 wherein the connector comprises an elastomer.

27. The anatomical brace according to claim 23 wherein said first end of said tensioner is elastic and said second end of said tensioner is substantially inelastic.

28. The anatomical brace according to claim 23 wherein said first end of said tensioner is adjustably mounted to said distal segment of said hinge mechanism.

29. The anatomical brace according to claim 23 wherein said second end of said tensioner is adjustably mounted to the distal portion of the brace body.

30. The anatomical brace according to claim 22 wherein said brace body comprises a flexible sheet material.

31. The anatomical brace according to claim 30 wherein said flexible sheet material comprises at least one from the group consisting of a woven fabric and a synthetic rubber.

32. The anatomical brace according to claim 31 wherein said flexible sheet material comprises neoprene.

33. The anatomical brace according to claim 22 wherein said anatomical brace is configured so that, when said anatomical brace is mounted to the knee of a patient, and when the knee of the patient thereafter moves to full flexion, said anatomical brace does not bunch in the back of said anatomical brace and cause tightness in the back of the knee of the patient.

34. The anatomical brace according to claim 22 wherein said pivot of said hinge mechanism comprises a central disk-shaped body to which said distal segment of said hinge mechanism and said proximal segment of said hinge mechanism are pivotally attached.

35. The anatomical brace according to claim 22 wherein said pivot of said hinge mechanism comprises one from the group consisting of a rivet pivot and a screw pivot.

36. An anatomical brace for selectively applying force to a selected portion of the anatomy of a patient during joint articulation, wherein the joint is characterized by a first bone, a second bone, a first side, a second side, a front side and a rear side, the anatomical brace comprising:

a brace body comprising a first portion for securement about the first bone and a second portion for securement about the second bone;

a hinge mechanism comprising a first segment connected to the first portion of the brace body on the first side of the joint, a second segment connected to the second portion of the brace body on the first side of the joint, and a pivot for pivotally connecting the first segment of the hinge mechanism to the second segment of the hinge mechanism; and a tensioner, the tensioner having a first portion secured to the first segment of the hinge mechanism, a second portion extending along the rear side of the pivot, a third portion extending along the second segment of the hinge mechanism and a fourth portion secured to the first portion of the brace body;

the anatomical brace being configured such that, when the first portion of the brace body is secured to the first bone and the second portion of the brace body is secured to the second bone, with the hinge mechanism being located on the first side of the joint, and when the joint thereafter moves to full extension, the tensioner is tensioned, such that the tensioner and the first portion of the brace body apply a force to the selected anatomy of the patient so as to urge the selected anatomy of the patient in the direction of the hinge mechanism, and when the joint thereafter moves to full flexion, the tensioner is relaxed, so that the force is relaxed.

37. The anatomical brace according to claim 36 wherein the tensioner comprises a cable and a connector attached to the cable.

38. The anatomical brace according to claim 37 wherein the cable comprises a metallic or plastic material and the connector comprises a non-metallic material.

39. The anatomical brace according to claim 37 wherein the connector has a variable length.

40. The anatomical brace according to claim 37 wherein the connector comprises an elastomer.

41. The anatomical brace according to claim 37 wherein said cable is elastic and said connector is substantially inelastic.

42. The anatomical brace according to claim 37 wherein said cable is adjustably mounted to said first segment of said hinge mechanism.

43. The anatomical brace according to claim 37 wherein said connector is adjustably mounted to the first portion of the brace body.

44. The anatomical brace according to claim 36 wherein said brace body comprises a flexible sheet material.

45. The anatomical brace according to claim 44 wherein said flexible sheet material comprises at least one from the group consisting of a woven fabric and a synthetic rubber.

46. The anatomical brace according to claim 45 wherein said flexible sheet material comprises neoprene.

47. The anatomical brace according to claim 36 wherein said anatomical brace is configured so that, when said anatomical brace is mounted to the joint of a patient, and when the joint of the patient thereafter moves to full flexion, said anatomical brace does not bunch in the back of said anatomical brace and cause tightness in the back of the joint of the patient.

48. The anatomical brace according to claim 36 wherein said pivot of said hinge mechanism comprises a central disk-shaped body to which said first segment of said hinge mechanism and said second segment of said hinge mechanism are pivotally attached.

49. The anatomical brace according to claim 36 wherein said pivot of said hinge mechanism comprises one from the group consisting of a rivet pivot and a screw pivot.

* * * * *